US008450057B2

(12) United States Patent
Gordon et al.

(10) Patent No.: US 8,450,057 B2
(45) Date of Patent: May 28, 2013

(54) DIAGNOSTIC TESTS USING GENE EXPRESSION RATIOS

(75) Inventors: Gavin J. Gordon, West Newbury, MA (US); Raphael Bueno, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 733 days.

(21) Appl. No.: 12/310,179

(22) PCT Filed: Aug. 8, 2007

(86) PCT No.: PCT/US2007/017604
§ 371 (c)(1),
(2), (4) Date: Sep. 15, 2009

(87) PCT Pub. No.: WO2008/021115
PCT Pub. Date: Feb. 21, 2008

(65) Prior Publication Data
US 2010/0028876 A1 Feb. 4, 2010

Related U.S. Application Data

(60) Provisional application No. 60/837,570, filed on Aug. 14, 2006.

(51) Int. Cl.
*C12Q 1/68* (2006.01)
*G01N 33/53* (2006.01)

(52) U.S. Cl.
USPC .............................................. 435/6.1; 435/7.1

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 5,770,176 A | 6/1998 | Nargessi | |
| 5,840,484 A | 11/1998 | Seilhamer et al. | |
| 6,040,138 A | 3/2000 | Lockhart et al. | |
| 2003/0219760 A1* | 11/2003 | Gordon et al. | 435/6 |
| 2009/0104617 A1 | 4/2009 | Gordon et al. | |

FOREIGN PATENT DOCUMENTS

| | | |
|---|---|---|
| WO | WO 00/55633 A2 | 9/2000 |
| WO | WO 03/021229 A2 | 3/2003 |

OTHER PUBLICATIONS

Tockman et al (Cancer Res., 1992, 52:2711s-2718s).*
Still et al (The Prostate, Jan. 2000, 42:18-25).*
Gordon et al (Cancer Research, 2002; 62: 4963-4967).*
Zumoff et al (J Clin Endocrinol Metab, Aug. 1980, 51(2):330-333).*
Alizadeh et al., Distinct types of diffuse large B-cell lymphoma identified by gene expression profiling. Nature. Feb. 3, 2000;403(6769):503-11.
Ara et al., Determination of imbalance between MMP-2 and TIMP-2 in human neuroblastoma by reverse-transcription polymerase chain reaction and its correlation with tumor progression. J Pediatr Surg. Mar. 2000;35(3):432-7.
Assersohn et al., The feasibility of using fine needle aspiration from primary breast cancers for cDNA microarray analyses. Clin Cancer Res. Mar. 2002;8(3):794-801.
Beer et al., Gene-expression profiles predict survival of patients with lung adenocarcinoma. Nat Med. Aug. 2002;8(8):816-24. Epub Jul. 15, 2002.
Bhattacharjee et al., Classification of human lung carcinomas by mRNA expression profiling reveals distinct adenocarcinoma subclasses. Proc Natl Acad Sci U S A. Nov. 20, 2001;98(24):13790-5.
Borczuk et al., Molecular signatures in biopsy specimens of lung cancer. Am J Respir Crit Care Med. Jul. 15, 2004;170(2):167-74. Epub Apr. 15, 2004.
Bueno et al., A diagnostic test for prostate cancer from gene expression profiling data. J Urol. Feb. 2004;171(2 Pt 1):903-6.
Calvo et al., Altered HOX and WNT7A expression in human lung cancer. Proc Natl Acad Sci U S A. Nov. 7, 2000;97(23):12776-81.
Chhieng et al., Calretinin staining pattern aids in the differentiation of mesothelioma from adenocarcinoma in serous effusions. Cancer. Jun. 25, 2000;90(3):194-200.
Clark et al., Genomic analysis of metastasis reveals an essential role for RhoC. Nature. Aug. 3, 2000;406(6795):532-5.
Crnogorac-Jurcevic et al., Gene expression profiles of pancreatic cancer and stromal desmoplasia. Oncogene. Nov. 1, 2001;20(50):7437-46.
Dhanasekaran et al., Delineation of prognostic biomarkers in prostate cancer. Nature. Aug. 23, 2001;412(6849):822-6.
Di Loreto et al., TTF-1 protein expression in pleural malignant mesotheliomas and adenocarcinomas of the lung. Cancer Lett. Feb. 13, 1998;124(1):73-8.
Dudoit et al., Comparison of discrimination methods for the classification of tumors using gene expression data. J Am Stat Assoc. 2002; 97(457):77-87.
Fodor, DNA sequencing: massively parallel genomics. Science. Jul. 18, 1997;277(5324): 393-395.
Frank et al., Identification of a differential expression of two cDNAs between malignant mesothelioma and normal mesothelial cells using the RNA fingerprint method. Tumour Biol. 1998;19(3):153-9.
Frank et al., Identification of genes involved in human mesothelial cancer progression using a modified differential display technique. Cancer Lett. Jan. 16, 1998;123(1):7-14.
Garber et al., Diversity of gene expression in adenocarcinoma of the lung. Proc Natl Acad Sci U S A. Nov. 20, 2001;98(24):13784-9. Epub Nov. 13, 2001. Erratum in: Proc Natl Acad Sci U S A Jan. 22, 2002;99(2):1098.

(Continued)

*Primary Examiner* — Sean Aeder
(74) *Attorney, Agent, or Firm* — Wolf, Greenfield & Sacks, P.C.

(57) ABSTRACT

The invention provides methods for diagnosing biological states or conditions based on ratios of gene expression data from cell or tissue samples, such as cancer cell or tissue samples. The invention also provides sets of genes that are expressed differentially in normal and cancer lung cells and tissues. These sets of genes can be used to discriminate between normal and malignant cells or tissues, and between classes of malignant cells or tissues. Accordingly, diagnostic assays for classification of tumors, prediction of tumor outcome, selecting and monitoring treatment regimens and monitoring tumor progression/regression also are provided.

15 Claims, No Drawings

OTHER PUBLICATIONS

Goetz et al., A two-gene expression ratio of homeobox 13 and interleukin-17B receptor for prediction of recurrence and survival in women receiving adjuvant tamoxifen. Clin Cancer Res. Apr. 1, 2006;12(7 Pt 1):2080-7.

Gohji et al., Serum matrix metalloproteinase-2 and its density in men with prostate cancer as a new predictor of disease extension. Int J Cancer. Feb. 20, 1998;79(1):96-101.

Golub et al., Molecular classification of cancer: class discovery and class prediction by gene expression monitoring. Science. Oct. 15, 1999;286(5439):531-7.

Gordon et al., A prognostic test for adenocarcinoma of the lung from gene expression profiling data. Cancer Epidemiol Biomarkers Prev. Sep. 2003;12(9):905-10.

Gordon et al., Differential diagnosis of solitary lung nodules with gene expression ratios. J Thorac Cardiovasc Surg. Sep. 2006;132(3):621-7.

Gordon et al., Translation of microarray data into clinically relevant cancer diagnostic tests using gene expression ratios in lung cancer and mesothelioma. Cancer Res. Sep. 1, 2002;62(17):4963-7.

Gordon et al., Using gene expression ratios to predict outcome among patients with mesothelioma. J Natl Cancer Inst. Apr. 16, 2003;95(8):598-605.

Gordon et al., Validation of genomics-based prognostic tests in malignant pleural mesothelioma. Clin Cancer Res. Jun. 15, 2005;11(12):4406-14.

Granville et al., An overview of lung cancer genomics and proteomics. Am J Respir Cell Mol Biol. Mar. 2005;32(3):169-76.

Groskopf et al., APTIMA PCA3 molecular urine test: development of a method to aid in the diagnosis of prostate cancer. Clin Chem. Jun. 2006;52(6):1089-95. Epub Apr. 20, 2006.

Groskopf et al., PCA3 Molecular Urine Assay: Characterization of a Method to Aid in the Diagnosis of Prostate Cancer, Poster 2006 European Association of Urology, Paris France.

Gullans et al., Of microarrays and meandering data points. Nat Genet. Sep. 2000;26(1):4-5.

Gwynne et al., Microarray Analysis: the next revolution in Molecular Biology. Science eMartketplace. Science. Aug. 6, 1999. (science.org/feature/e-market/benchtop/micro.shl).

Hedenfalk et al., Gene-expression profiles in hereditary breast cancer. N Engl J Med. Feb. 22, 2001;344(8):539-48.

Hofmann et al., Discrimination of human lung neoplasm from normal lung by two target genes. Am J Respir Crit Care Med. Sep. 1, 2004;170(5):516-9.

Hough et al., Large-scale serial analysis of gene expression reveals genes differentially expressed in ovarian cancer. Cancer Res. Nov. 15, 2000;60(22):6281-7.

Hsiao et al., A compendium of gene expression in normal human tissues. Physiol Genomics. Dec. 21, 2001;7(2):97-104.

Jansen et al., Re: Limits of predictive models using microarray data for breast cancer clinical treatment outcome. J Natl Cancer Inst. Dec. 21, 2005;97(24):1851-2; author reply 1852-3.

Kettunen et al., Gene expression profiling of malignant mesothelioma cell lines: cDNA array study. Int J Cancer. Feb. 15, 2001;91(4):492-6.

Khan et al., Classification and diagnostic prediction of cancers using gene expression profiling and artificial neural networks. Nat Med. Jun. 2001;7(6):673-9.

LaPointe et al., Gene expression profiling identifies clinically relevant subtypes of prostate cancer. Proc Natl Acad Sci U S A. Jan. 20, 2004;101(3):811-6. Epub Jan. 7, 2004.

Lee et al., Microarray profiling of isolated abdominal subcutaneous adipocytes from obese vs non-obese Pima Indians: increased expression of inflammation-related genes. Diabetologia. Sep. 2005;48(9):1776-83. Epub Jul. 30, 2005.

Liu et al., Expression and activity of matrix metalloproteases in human malignant mesothelioma cell lines. Int J Cancer. Mar. 1, 2001;91(5):638-43.

Lozano et al., Immunocytochemistry in the differential diagnosis of serous effusions: a comparative evaluation of eight monoclonal antibodies in *Papanicolaou* stained smears. Cancer. Feb. 25, 2001;93(1):68-72.

Ma et al., A two-gene expression ratio predicts clinical outcome in breast cancer patients treated with tamoxifen. Cancer Cell. Jun. 2004;5(6):607-16.

Mohr et al., [Gene expression profiling in human mesothelioma cells using DNA microarray and high-density filter array technologies] Bull Cancer. Mar. 2001;88(3):305-13. French.

Mountain, Revisions in the International System for Staging Lung Cancer. Chest. Jun. 1997;111(6):1710-7.

O'Dell et al., Associations of IGF2 ApaI RFLP and INS VNTR class I allele size with obesity. Eur J Hum Genet. Oct.-Nov. 1999;7(7):821-7.

Ordóñez, The immunohistochemical diagnosis of epithelial mesothelioma. Hum Pathol. Mar. 1999;30(3):313-23.

Ordóñez, The value of antibodies 44-3A6, SM3, HBME-1, and thrombomodulin in differentiating epithelial pleural mesothelioma from lung adenocarcinoma: a comparative study with other commonly used antibodies. Am J Surg Pathol. Dec. 1997;21(12):1399-408.

Paramothayan et al., New criteria for the differentiation between transudates and exudates. J Clin Pathol. Jan. 2002;55(1):69-71.

Perou et al., Molecular portraits of human breast tumours. Nature. Aug. 17, 2000;406(6797):747-52.

Pomeroy et al., Prediction of central nervous system embryonal tumour outcome based on gene expression. Nature. Jan. 24, 2002;415(6870):436-42.

Quackenbush, Computational analysis of microarray data. Nat Rev Genet. Jun. 2001;2(6):418-27.

Reid et al., Limits of predictive models using microarray data for breast cancer clinical treatment outcome. J Natl Cancer Inst. Jun. 15, 2005;97(12):927-30.

Reimer et al., FasL:Fas ratio—a prognostic factor in breast carcinomas. Cancer Res. Feb. 15, 2000;60(4):822-8.

Rihn et al., Differential gene expression in mesothelioma. FEBS Lett. Sep. 1, 2000;480(2-3):95-100.

Rosenwald et al., The use of molecular profiling to predict survival after chemotherapy for diffuse large-B-cell lymphoma. N Engl J Med. Jun. 20, 2002;346(25):1937-47.

Sandhu et al., mRNA expression patterns in different stages of asbestos-induced carcinogenesis in rats. Carcinogenesis. May 2000;21(5):1023-9.

Sato et al., Differential diagnosis of mesothelial and ovarian cancer cells in ascites by immunocytochemistry using Ber-EP4 and calretinin. Acta Cytol. May-Jun. 2000;44(3):485-8.

Shipp et al., Diffuse large B-cell lymphoma outcome prediction by gene-expression profiling and supervised machine learning. Nat Med. Jan. 2002;8(1):68-74.

Sotiriou et al., Gene expression profiles derived from fine needle aspiration correlate with response to systemic chemotherapy in breast cancer. Breast Cancer Res. 2002;4(3):R3. Epub Mar. 20, 2002.

Still et al., Localization and quantification of mRNA for matrix metalloproteinase-2 (MMP-2) and tissue inhibitor of matrix metalloproteinase-2 (TIMP-2) in human benign and malignant prostatic tissue. Prostate. Jan. 2000;42(1):18-25.

Su et al., Molecular classification of human carcinomas by use of gene expression signatures. Cancer Res. Oct. 15, 2001;61(20):7388-93.

Sugarbaker et al., Extrapleural pneumonectomy in the multimodality therapy of malignant pleural mesothelioma. Results in 120 consecutive patients. Ann Surg. Sep. 1996;224(3):288-94; discussion 294-6.

Sugarbaker et al., Node status has prognostic significance in the multimodality therapy of diffuse, malignant mesothelioma. J Clin Oncol. Jun. 1993;11(6):1172-8.

Sugarbaker et al., Resection margins, extrapleural nodal status, and cell type determine postoperative long-term survival in trimodality therapy of malignant pleural mesothelioma: results in 183 patients. J Thorac Cardiovasc Surg. Jan. 1999;117(1):54-63; discussion 63-5.

Sun et al., Upregulation of 9 genes, including that for thioredoxin, during epithelial differentiation of mesothelioma cells. Differentiation. Dec. 2000;66(4-5):181-8.

Tusher et al., Significance analysis of microarrays applied to the ionizing radiation response. Proc Natl Acad Sci U S A. Apr. 24, 2001;98(9):5116-21.

Vachani et al., A 10-gene classifier for distinguishing head and neck squamous cell carcinoma and lung squamous cell carcinoma. Clin Cancer Res. May 15, 2007;13(10):2905-15.

Van 'T Veer et al., Gene expression profiling predicts clinical outcome of breast cancer. Nature. Jan. 31, 2002;415(6871):530-6.

Virtaneva et al., Expression profiling reveals fundamental biological differences in acute myeloid leukemia with isolated trisomy 8 and normal cytogenetics. Proc Natl Acad Sci U S A. Jan. 30, 2001;98(3):1124-9.

Wang et al., Monitoring gene expression profile changes in ovarian carcinomas using cDNA microarray. Gene. Mar. 18, 1999;229(1-2):101-8.

Warrington et al., Comparison of human adult and fetal expression and identification of 535 housekeeping/maintenance genes. Physiol Genomics. Apr. 27, 2000;2(3):143-7.

Welsh et al., Analysis of gene expression identifies candidate markers and pharmacological targets in prostate cancer. Cancer Res. Aug. 15, 2001;61(16):5974-8.

Welsh et al., Analysis of gene expression profiles in normal and neoplastic ovarian tissue samples identifies candidate molecular markers of epithelial ovarin cancer. Proc Natl Acad Sci U S A. Jan. 30, 2001;98(3):1176-81.

Zumoff et al., Sex differences in the twenty-four-hour mean plasma concentrations of dehydroisoandrosterone (DHA) and dehydroisoandrosterone sulfate (DHAS) and the DHA to DHAS ratio in normal adults. J Clin Endocrinol Metab. Aug. 1980;51(2):330-3.

* cited by examiner

DIAGNOSTIC TESTS USING GENE EXPRESSION RATIOS

RELATED APPLICATIONS

This application is a national stage filing under 35 U.S.C. §371 of international application PCT/US2007/017604, filed Aug. 8, 2007, which was published under PCT Article 21(2) in English, and claims the benefit under 35 U.S.C. §119(e) of U.S. provisional application 60/837,570, filed Aug. 14, 2006, the disclosures of which are incorporated in their entirety herein by reference.

FIELD OF THE INVENTION

The invention relates to methods for diagnosing conditions, predicting prognoses and optimizing treatment strategies using ratios of gene expression data. The invention also relates to nucleic acid markers for cancer, particularly for diagnosing cancer and for distinguishing among different types of cancer, particularly lung cancer.

BACKGROUND OF THE INVENTION

Although much progress has been made toward understanding the biological basis of cancer and in its diagnosis and treatment, it is still one of the leading causes of death in the United States. Inherent difficulties in the diagnosis and treatment of cancer include among other things, the existence of many different subgroups of cancer and the concomitant variation in appropriate treatment strategies to maximize the likelihood of positive patient outcome.

Subclassification of cancer has typically relied on the grouping of tumors based on tissue of origin, histology, cytogenetics, immunohistochemistry, and known biological behavior. The pathologic diagnosis used to classify the tumor taken together with the stage of the cancer is then used to predict prognosis and direct therapy. However, current methods of cancer classification and staging are not completely reliable.

Gene expression profiling using microarrays is likely to result in improvements in cancer classification and prediction of prognosis (Golub et al., Science 286: 531-537, 1999; Perou et al., Nature 406: 747-752, 2000; Hedenfalk et al., N Engl J Med 344: 539-548, 2001; and Khan et al., Nat Med 7: 673-679, 2001). Still, the wealth of information garnered using microarrays has, thus far, not yielded effective clinical applications. Global expression analysis has led to the development of sophisticated computer algorithms seeking to extend data analysis beyond simple expression profiles (Quackenbush, Nat Rev Genet 2, 418-427, 2001; Khan et al. Nat Med 7, 673-679, 2001). At this time, however, no clear consensus exists regarding which computational tools are optimal for the analysis of large gene expression profiling data sets, particularly in the clinical setting. Moreover, many of these bioinformatics tools under development and testing are quite complex leaving the practical use of microarray data beyond the scope of many biomedical scientists and/or clinicians. With rare exceptions (e.g. PSA and prostate cancer), it is generally assumed that expression levels of any one gene are insufficient in the diagnosis and/or prognosis of cancer. However, it is equally erroneous to assume a priori that the expression profiles of large numbers of genes are explicitly required for this purpose.

It is difficult to predict from standard clinical and pathologic features the clinical course of cancer. However, it is very important in the treatment of cancer to select and implement an appropriate combination of therapeutic approaches. The available methods for designing strategies for treating cancer patients are complex and time consuming. The wide range of cancer subgroups and variations in disease progression limit the predictive ability of the healthcare professional. In addition, continuing development of novel treatment strategies and therapeutics will result in the addition of more variables to the already complex decision-making process involving matching the cancer patient with a treatment regimen that is appropriate and optimized for the cancer stage, tumor growth rate, and other factors central to the individual patient's prognosis. Because of the critical importance of selecting appropriate treatment regimens for cancer patients, the development of guidelines for treatment selection is of key interest to those in the medical community and their patients. Thus, there presently is a need for objective, reproducible, and sensitive methods for diagnosing cancer, predicting cancer patient prognosis and outcome, and selecting and monitoring optimal treatment regimens.

SUMMARY OF THE INVENTION

Gene expression profiling using microarrays and complex bioinformatics tools has been used to successfully diagnose cancer. Unfortunately, these models are difficult to assess clinically because they rely on measuring the expression levels of relatively large numbers of genes using costly data acquisition platforms and sophisticated algorithms/software. The invention is based on applicant's discovery that a select number of genes are differentially expressed among normal lung and different types of lung cancer. The Applicant used these genes to develop a new method to diagnose lung cancer based on analyzing the gene expression ratios. One of the advantages of the new method over the prior art is that it allows the analysis of more than two cell or tissue types. Thus, this new method not only determines the presence or absence of a cancer (e.g., type of lung cancer) but will also identify the type of lung cancer (e.g., type of lung cancer) among several types with high specificity and sensitivity. Another advantage of the new method is that it is suitable to be used with fine needle aspiration (FNA)-derived samples. The new method may also be used to predict prognosis and to optimize treatment.

The diagnostic and prognostic methods that were developed utilize gene expression data from a few genes through the use of expression level ratios and rationally chosen thresholds. The effectiveness of unit-less ratios in diagnosing cancer types was demonstrated and confirmed using real time quantitative reverse-transcriptase polymerase chain reaction (RT-PCR). This is a simple, but powerful, use of microarray data that can be easily adapted to a clinical setting to diagnose cancer (and non-cancer tissue or diseases) and predict patient outcome without complex computer software or hardware. Accordingly, diagnostic assays for classification of tumors, prediction of tumor outcome, selecting and monitoring treatment regimens, and monitoring tumor progression/regression can now be based on the ratios of expression of a small number of genes.

The gene expression ratio concept can be applied to diagnose or distinguish between cells or tissues in different biological states, such as distinguishing between or among cells or tissues from subjects having disease and not having disease, tissues or cells as being one of three or more tissue or cell type, subjects that vary in response to a pharmaceutical or that metabolize a pharmaceutical at different rates, subjects that vary in disease susceptibility or predisposition, and the like. Thus, a subject's prognosis or response to treatments, inter alia, can be determined through analysis of a limited set of genes in particular biological samples. Moreover, the gene expression data can be obtained from, and comparisons can be made between, a number of different methods including nucleic acid hybridization (e.g., microarrays) and nucleic acid amplification methods (e.g., RT-PCR).

According to one aspect of the invention, a method for identifying a cell or a tissue as being one of three or more cell or tissue types is provided. The method comprises determining the expression levels of a set of genes, wherein the set comprises at least one upregulated gene that is expressed in greater amounts in a first type of cell or tissue than in a second type(s) of cell or tissue and at least one downregulated gene that is expressed in lesser amounts in the first type of cell or tissue than in the second type(s) of cell or tissue. The method also includes calculating at least one ratio (R) of the expression level of the at least one upregulated gene (A) to the expression level of the at least one downregulated gene (B), wherein the at least one ratio (R) provides an identification of the cell or tissue as being one of three or more cell or tissue types. The ratios or combination of ratios for comparing the cells or tissues (first type, second type, third type of cell or tissue, or more) are different for each cell or tissue. In some preferred embodiments, the set of genes comprises three or more genes.

In some embodiments, the cell or tissue is a cancer cell or tissue. In some important embodiments, the ratio distinguishes between types of cancer cells or tissues.

Examples of cells or tissues include but are not limited to brain, nerve, skin, eye, pharynx, larynx, lung, heart, vascular, hematopoietic (e.g., white blood cell or red blood cell), breast, liver, pancreas, spleen, esophagus, gall bladder, stomach, intestine, colon, kidney, urinary bladder, ovary, uterus, cervix, prostate, muscle, bone, thyroid, parathyroid, adrenal, and pituitary cells or tissues. In some preferred embodiments, the cell or tissue is a lung cell or tissue.

According to another aspect of the invention, a method for identifying a lung cell or tissue is provided. The method comprises determining the expression levels of the set of two or more genes disclosed in Table 1, 4, 5, 6, or 7 wherein the set comprises at least one upregulated gene that is expressed in greater amounts in a first type of lung cell or tissue than in a second type of lung cell or tissue and at least one downregulated gene that is expressed in lesser amounts in the first type of lung cell or tissue than in the second type of lung cell or tissue. The method also includes calculating at least one ratio (R) of the expression level of the at least one upregulated gene (A) to the expression level of the at least one down-regulated gene (B), wherein the at least one ratio (R), provides an identification of the lung cell or tissue.

According to another aspect of the invention, a method for determining prognosis or outcome of a lung cancer subject is provided. The method comprises determining the expression levels of a set of two or more genes disclosed in Table 1, 4, 5, 6, or 7 wherein the set comprises at least one upregulated gene that is expressed in greater amounts in a sample from a lung cancer subject having a good prognosis or outcome than in a sample from a lung cancer subject having a poor prognosis or outcome and at least one downregulated gene that is expressed in lesser amounts in the sample from the lung cancer subject having a good prognosis or outcome than in the sample from the lung cancer subject having a poor prognosis or outcome. The method also includes calculating at least one ratio (R) of the expression level of the at least one upregulated gene (A) to the expression level of the at least one downregulated gene (B), wherein the at least one ratio (R) is indicative of the prognosis or outcome of the lung cancer subject.

According to yet another aspect of the invention, a kit for cancer diagnosis is provided. The kit comprises a set of one or more ratios applicable to the analysis of gene expression data, wherein the ratio is calculated from the expression levels of at least one upregulated gene disclosed in Table 1, 4, 5, 6, or 7 that is expressed in greater amounts in a first type of cell or tissue than in a second type of cell or tissue and at least one downregulated gene that is expressed in lesser amounts in the first type of cell or tissue than in the second type of cell or tissue. In some embodiments, the kit also includes instructions for the use of the one or more ratios in the cancer diagnosis.

According to still another aspect of the invention, a lung cancer diagnostic system is provided. The diagnostic system comprises a measurement device that measures gene expression level data of a set of two or more genes disclosed in Table 1, 4, 5, 6, or 7 wherein the set comprises at least one upregulated gene that is expressed in greater amounts in a first type of lung cell or tissue than in a second type of lung cell or tissue and at least one downregulated gene that is expressed in lesser amounts in the first type of lung cell or tissue than in the second type of lung cell or tissue. The diagnostic system includes a data transformation device that acquires the gene expression data from the measurement device and performs data transformation to calculate a ratio of the gene expression levels of the upregulated and downregulated genes.

In some embodiments, the data transformation device selects gene expression data of a selected set of genes from the measurement device for calculating the ratio of the selected set of genes, wherein the ratio calculated from the gene expression data of the selected set of genes is diagnostic for a selected lung cancer.

In some embodiments, the diagnostic system further comprises a user interface output device to output the ratio to a user. The diagnostic system may further comprise a database of ratios of gene expression that are diagnostic for lung cancers and a comparison device that compares the ratio calculated from the measured gene expression to the diagnostic ratios stored in the database and outputs the comparison to the user interface output device.

In some embodiments, the diagnostic system includes a database of treatment information for specific lung cancers, wherein the comparison device identifies treatment information in the database for the specific cancer for which the diagnostic ratio matches the calculated ratio, and wherein the comparison outputs the treatment information to the user interface output device.

According to yet another aspect of the invention, a method for diagnosing lung cancer in a subject suspected of having lung cancer is provided. The method comprises obtaining a sample from the subject, determining the expression of a set of nucleic acid molecules or expression products thereof in the sample, wherein the set of nucleic acid molecules comprises at least two nucleic acid molecules disclosed in Table 1, 4, 5, 6, or 7.

The sample may be a tissue sample (preferably lung tissue) or a fine needle aspirate (FNA) from the lung. The tissue sample may be suspected of being cancerous.

In some important embodiments, the set of nucleic acid molecules comprises at least 3, 4, 5 10, 12, 15, 20, 25 or more nucleic acid molecules disclosed in Table 1, 4, 5, 6, or 7.

In some embodiments, the method further comprises determining the expression of the set of nucleic acid molecules or expression products thereof in a control sample, and comparing the expression of the set of nucleic acid molecules or expression products thereof in the sample suspected of being cancerous and the control sample. In certain embodiments, the method further comprises calculating a ratio of the expression of at least two genes among the set of nucleic acid molecules.

According to still another aspect of the invention, a method for selecting a course of treatment of a subject having or suspected of having lung cancer is provided. The method comprises obtaining from the subject a sample suspected of being cancerous, determining the expression of a set of nucleic acid molecules disclosed in the Table 1, 4, 5, 6, or 7 or expression products thereof which are differentially expressed in lung cancer samples, and selecting a course of treatment appropriate to the lung cancer of the subject. The sample may be a tissue sample or a fine needle aspirate (FNA) from the lung.

In some embodiments, the method further comprises calculating a ratio of the expression of at least two genes among the set of nucleic acid molecules or expression products thereof. The method may further comprise determining the expression of the set of nucleic acid molecules or expression products thereof in a control sample.

In another aspect of the invention, a method for evaluating treatment of lung cancer is provided. The method comprises obtaining a first determination of the expression of a set of nucleic acid molecules disclosed in Table 1, 4, 5, 6, or 7 or expression products thereof, which are differentially expressed in a lung cancer sample from a subject undergoing treatment for cancer, obtaining a second determination of the expression of the set of nucleic acid molecules, or expression products thereof, in a second lung cancer sample from the subject after obtaining the first determination, and comparing the first determination of expression to the second determination of expression as an indication of evaluation of the treatment.

In some embodiments, the determinations of expressions are used to calculate at least one ratio of gene expression. The method may further comprise determining the expression of a set of nucleic acid markers which are differentially expressed in a control sample.

According to a further aspect of the invention, a solid-phase nucleic acid molecule array is provided which consists essentially of at least two nucleic acid molecules disclosed in Table 1, 4, 5, 6 or 7 fixed to a solid substrate. In some embodiments, the solid-phase nucleic acid molecule array further comprises at least one control nucleic acid molecule. In some preferred embodiments, the set of nucleic acid molecules comprises at least 3, 4, 5, 10, 12, 15, 20, 25 or more nucleic acid molecules disclosed in Table 1, 4, 5, 6, or 7.

According to yet another aspect of the invention, a solid-phase protein microarray is provided which comprises at least two antibodies or antigen-binding fragments thereof that specifically bind at least two different polypeptides selected from the group consisting of polypeptides encoded by the nucleic acid molecules disclosed in Table 1, 4, 5, 6 or 7 fixed to a solid substrate. In some embodiments, the protein microarray further comprises at least one control polypeptide molecule.

In some preferred embodiments, the antibodies are monoclonal antibodies. In some other preferred embodiments, the antibodies are polyclonal antibodies.

Methods for identifying lead compounds for a pharmacological agent useful in the treatment of lung cancer are provided in another aspect of the invention. The methods comprise contacting a lung cancer cell or tissue with a candidate pharmacological agent, determining the expression of a set of nucleic acid molecules in the lung cancer cell or tissue sample under conditions which, in the absence of the candidate pharmacological agent, permit a first amount of expression of the set of nucleic acid molecules wherein the set of nucleic acid molecules comprises at least two nucleic acid molecules selected from the nucleic acid molecules disclosed in Table 1, 4, 5, 6, or 7 and detecting a test amount of the expression of the set of nucleic acid molecules, wherein a decrease in the test amount of expression in the presence of the candidate pharmacological agent relative to the first amount of expression indicates that the candidate pharmacological agent is a lead compound for a pharmacological agent which is useful in the lung cancer. In some embodiments, the method further comprises calculating a ratio of gene expression.

The following embodiments apply equally to the various aspects of the invention set forth herein unless indicated otherwise.

The lung cell or tissue may be normal lung cell or tissue, small cell lung cancer, adenocarcinoma, squamous cell carcinoma, metastatic cancer, pulmonary carcinoid, large cell lung cancer, bronchioalveolar carcinoma, or non-cancerous diseased lung cell or tissue. The metastatic cancer may be of lung cell or tissue origin or of non-lung cell or tissue origin. Examples of noncancerous diseased lung cell or tissue include but are not limited to dysplasia, metaplasia, carcinoma-in-situ, and pulmonary fibrosis.

The cell may be in a tissue sample or in a fine needle aspirate (FNA), preferably from the lung.

In certain embodiments, the upregulated and downregulated genes are selected as having statistically significant differences in mean expression levels. In some preferred embodiments, there is at least a 2-fold difference in mean expression levels between the at least one upregulated gene (A) and the at least one downregulated gene (B).

Two or more expression ratios ($R_1, R_2, \ldots, R_n$) may be calculated. In some embodiments, two or more expression ratios ($R_1, R_2, \ldots, R_n$) are combined. The step of combining the two or more expression ratios may comprise calculating the geometric mean of the two or more expression ratios using the following formula: $(R_1, R_2 \ldots R_n)^{1/n}$, wherein R represents a single ratio value. For example, 2, 3, 4, 5, 6, 7, 8, 9, 10 or more ratios can be calculated and used as described herein. One way of identifying a cell, tissue or sample is to select the identity of the sample as corresponding to the cell or tissue with the highest geometric mean.

The ratio may be calculated by division of the expression level of one upregulated gene by the expression level of one downregulated gene using the formula A/B. In some embodiments, the ratio(s) is calculated by division of the expression levels of two or more upregulated genes ($A_1, A_2, \ldots, A_n$) by the expression level of one downregulated gene (B) using the formula $((A_1, A_2 \ldots A_n)^{1/n}/B)$. In some other embodiments, the ratio(s) is calculated by division of the expression level of one upregulated gene (A) by the expression levels of two or more downregulated genes ($B_1, B_2, \ldots, B_m$) using the formula $(A/(B_1 B_2 \ldots B_m)^{1/m})$. In some embodiments, the ratio(s) is calculated by division of the expression levels of two or more upregulated genes ($A_1, A_2, \ldots, A_n$) by the expression levels of two or more down-regulated genes ($B_1, B_2, \ldots, B_m$) using the formula $(A_1 A_2 \ldots A_n)^{1/n}/(B_1 B_2 \ldots B_m)^{1/m}$.

In some embodiments, the method comprises transforming the expression level data for the upregulated and/or downregulated genes prior to calculating the ratio.

The expression levels may be determined by nucleic acid hybridization, nucleic acid amplification, or an immunological method. One example of a nucleic acid hybridization may be performed using a solid-phase nucleic acid molecule array. One example of a nucleic acid amplification method is real-time quantitative RT-PCR.

Examples of the immunological methods for determining expression levels include solid-phase antibody array, ELISA or ELISPOT assays.

These and other aspects of the invention, as well as various advantages and utilities, will be more apparent with reference to the detailed description of the invention. Each aspect of the invention can encompass various embodiments.

DETAILED DESCRIPTION OF THE INVENTION

Gene expression profiling using high density oligonucleotide arrays has figured prominently in recent studies using gene expression patterns in cancer to improve diagnosis and subclassification. Specifically, microarrays have been used to distinguish between acute myeloid leukemia (AML) and acute lymphoblastic leukemia (ALL) (Golub et al., Science 286: 531-537, 1999), to explore molecular differences within the AML group of diseases (Virtaneva et al., Proc Natl Acad Sci USA 98, 1124-1129, 2001), to identify subclasses of breast cancer (Perou et al., Nature 406: 747-752, 2000) and ovarian carcinoma (Welsh et al., Cancer Res 61: 5974-5978, 2001), and to define the metastatic phenotype of melanoma (Clark et al., Nature 406, 532-535 2000).

Although mnicroarray-based analysis of gene expression in cancer has yielded a wealth of information, effective clinical applications have not followed for several reasons. There are no universally accepted and applicable computational methods to analyze microarray data (Quackenbush, Nat Rev Genet 2, 418-427, 2001). Also, studies utilizing microarrays have lacked a comprehensive clinical database linking patient characteristics to their tumors' gene expression patterns. Furthermore, the prospect of having to use large numbers of genes to diagnose a disease subclass would require a relatively expensive analytical approach such as microarrays. Finally, sophisticated computer algorithms currently used for analysis of microarrays (Quackenbush, Nat Rev Genet 2, 418-427, 2001; D et al., Nat Med 7: 673-679, 2001) have placed the practical use of the resulting data beyond the reach of many biomedical scientists. We addressed these limitations in a recently described method for translating gene expression profiling data into clinically relevant tests using ratios of gene expression in multiple cancers. (Gordon et al., Clin Cancer Res 11:4406-14, 2005; Gordon et al., Cancer Epidemiol Biomarkers Prev 12:905-10, 2003; Gordon et al., Cancer Res 62:4963-67, 2002; Gordon et al., J Natl Cancer Inst; 95:598-6058, 2003; Bueno et al., J Urol 171:903-06, 2004; and WO 03/021229).

In contrast to many microarray-based studies seeking to compare gene expression patterns between two or more predefined groups, unsupervised clustering was first used for class discovery in malignant pleural mesothelioma (MPM). In this way, the introduction of experimental bias that follows from assuming that tumors of the same histological subtype necessarily possess similar gene expression profiles was avoided. By extension, prognostic genes were identified based on differential expression levels between tumors that were members of the two subclasses with the best and worst prognoses, and not based simply on tumor histology.

Subclassification using unsupervised clustering also presents a more biologically relevant organization. It has been shown that similar tumor appearance in itself does not necessitate similar patterns of gene expression nor final clinical outcome. For example, it is not unusual for patients with lung cancers of identical histology, differentiation, location, and stage to have diverging survival (Mountain, Chest 111, 1710-1717, 1997).

Patient outcome depends on the phenotype of individual tissue (e.g., tumor) at the molecular level, and this is reflected directly in gene expression. The recent explosion of bioinformatics has facilitated exploration of complex patterns of gene expression in human tissues (Fodor, Science 277, 393-395 1997). However, exact relationships between gene expression patterns in cancer and clinical data remain largely undefined. Sophisticated computer algorithms have been recently developed which are capable of molecular diagnosis of tumors using the immense data sets generated by expression profiling (Khan et al., Nat Med 7: 673-679, 2001). Though valid, the widespread clinical applicability of these techniques in the foreseeable future is questionable.

Microarrays are evolving at a rapid pace but gene expression analysis in this manner remains an expensive endeavor. Therefore, comparing historical data to that obtained from new generation microarrays remains a priority for most investigators. Yet there are no satisfactory solutions to date that adequately address all of the normalization issues encountered when attempting to merge data from older microarrays, or those from multiple manufacturers. Examination of ratios of gene expression, as described herein, as opposed to absolute expression levels, also assists in the practical use of data from the older generation of commercially obtained microarrays.

The invention described herein is based, in part, on the identification of a set of genes that are differentially expressed in normal lung and multiple types of lung cancer that are diagnostic for the cancer and/or predictive of the clinical outcome of the cancer. In one aspect, ratios of gene expression are used as indicia of the lung cancer type, lung cancer class, and/or the lung cancer prognosis, all of which are useful for determining a course of treatment of a patient.

Changes in cell phenotype in cancer are often the result of one or more changes in the genome expression of the cell. For example, some genes are expressed in cancer cells, and not in normal cells. Other genes are expressed at higher or lower levels in cancer cells than in normal counterparts. In addition, certain genes are expressed in different levels in different subgroups of cancers, which have different prognoses and require different treatment regimens to optimize patient outcome. The differential expression of such genes can be examined by the assessment of nucleic acid or protein expression in the cancer tissue.

Gene expression ratios can be applied to various tissues to diagnose or distinguish between cells or tissues in different biological states and conditions, such as cells or tissues having or not having disease. One of the advantages of the new method over the prior art is that it allows the analysis of more than two cell or tissue types. Recent developments in gene expression analysis involve the use of microarrays to measure simultaneously the expression of hundreds or thousands of genes. Practical application of this technology requires that researchers or laboratories have a sophisticated knowledge of molecular biology to generate gene expression data, and of computer algorithms for analysis of the large quantities of data generated by the use of the microarrays. The requirements for such knowledge make the use of microarrays impractical in the clinical setting, and difficult even for research laboratories. In addition, one must account for differences in microarray architecture, sample preparation, and analytical equipment that captures the signals from the microarrays.

The use of gene expression ratios in the diagnosis and prediction of prognosis of a condition (e.g., cancer) overcomes several major obstacles to the clinical use of microarray data. The methodology described herein avoids the technical difficulties described above. It generates a simple numerical measure that can be used to predict various aspects of patient clinical data (such as histological subtype and survival) using a single patient biopsy sample. Since this non-linear function of gene expression is a unit-less number, expression levels can be measured using any reliable method such as quantitative RT-PCR or microarrays (nucleic acid or protein) regardless of the type of data capture equipment. Thus, the present invention permits the diagnosis of a condition (e.g., cancer) by clinical laboratories using standard equipment without the requirement for sophisticated data analysis.

Importantly, the diagnostic/prognostic accuracy of ratios permits an earlier definitive diagnosis using initial biopsy samples and reveals important clues about anticipated patient outcome prior to the assignment of treatment strategies. Unfortunately, standard pathological techniques for diagnosis may be inadequate due to a lack of suitable quantities of tissue. As a consequence, the histological subtype of the tumor or cancer initially diagnosed may not always be the same as that conclusively determined at the time of surgery. This makes it difficult, if not impossible, to stratify treatment based on histological subtyping by prevailing methods. Ratios obtained using tumor tissues taken at the time of initial biopsy can provide a firm diagnosis, determine subclass, and predict outcome after therapy when current pathological techniques are insufficient.

The invention also provides a new, powerful method of stratifying patients with disease (such as lung cancer). It has been previously documented that patients with the certain types of cells have a better prognosis than patients with other types (regardless of treatment strategy) and benefit from aggressive surgical resection. Such factors make it difficult to design clinical studies to explore alternative treatment strategies based on histological subtype.

A series of simple tests utilizing ratios of gene expression is proposed that can determine with a high degree of accuracy the correct tumor subtype/subclass (e.g., type of cancer), and the likely clinical outcome of the patient. This information can be produced from a small tissue biopsy and does not require major surgery. Such classification is useful in the development of meaningful clinical trials patients with different types or subtypes of conditions (e.g., lung cancer).

Expression ratios involving several genes that vary in expression between different sample types (e.g., cancer/non-cancer) were used to detect and differentially diagnose condition (e.g., lung cancer). Diagnostic and/or prognostic genes in general can be initially identified from microarray analysis and then be tested for clinical relevancy using simpler methods such as RT-PCR. To accomplish similar feats in other biological conditions or states, including other cancers, it may be necessary to use expression ratios including different mathematical combinations. The ratio concept described herein (e.g., for clinical use) is simply the relationship between the expression levels of multiple genes that vary in expression between two or more different sample types, i.e., samples that have different biological properties or were obtained from subjects having different phenotypes, such as cancer/non-cancer phenotypes, different cancer subtypes (e.g., different types of lung cancer), responsive/non-responsive to stimuli, susceptible/not susceptible to disease, different metabolic functions, etc. Non-linear unit-less ratios, in any form, can still remain simple if a relatively small number of genes are used in such a way as to not require complex computational software. Therefore, expression ratios of selected genes that vary in expression in two different biological samples may be used to translate complex data sets into simple tests that give clinically useful information for the diagnosis and prediction of prognosis of cancers.

Ratios of gene expression levels can be calculated from expression data of two or more genes at the mRNA level and or protein level. Expression levels of two or more isoforms or variants of the same gene (e.g., splice variants or post-translationally modified variants) also can be used in the ratios. In contrast to certain prior methods for comparing gene expression, which compared the expression levels of genes relative to a gene having substantially unchanging expression (e.g., a housekeeping gene), the present method compares the expression of two or more genes that differ in expression between tree or more biological states. Examples of this are demonstrated herein, wherein the expression levels of two or more genes that differ in expression among normal lung and multiple types of lung cancer, are used to calculate ratios that effectively predict the phenotype of unknown tissue samples.

The ratios can be simple ratios (e.g., x/y) or more complex ratios that include mathematical manipulation of gene expression levels, for example, $(x+a)/(y+b)$ or $x^3/y^3$, wherein x and y represent the expression level data for genes X and Y, and a and b can be either expression level data for genes A and D, or mathematical factors. The use of the ratios is not limited to any set of genes. Two, three, four, or more sets of genes may be required to provide an optimally accurate diagnosis of certain biological states or conditions (e.g., lung cancer or subtype of lung cancer) based on the expression of certain sets of genes. A total of 3, 4, 5, 6, or more genes and various ratios of them may be used. Further transformation of the data in the form of multiple gene expression ratios also can be performed. In certain preferred embodiments, the geometric mean of multiple gene ratios is calculated. The expression data used to calculate the ratios may be obtained using any art-known method for analyzing gene expression including microarrays (e.g., standard or custom arrays; nucleic acid, protein or antibody arrays), RT-PCR (preferably quantitative RT-PCR, such as real-time reverse transcriptase PCR) antibody or other immunoassay measurements, etc.

The ratios can be used to diagnose any condition having a genetic component in which two or more genes are differentially expressed in two or more (preferably three or more) biological states or conditions. Conditions include diseases, susceptibility to diseases, metabolic functions (e.g., variability in the metabolism of drugs), response to injury, responses to local cellular environments and the like. In preferred embodiments, the condition is a disease. For example, any disease that is characterized by (1) the relative increase in the expression of a first gene in a first disease state, and (2) the relative increase in the expression of a second gene in a second or third (or more) disease state or nondisease state, can be diagnosed using ratios of gene expression. Preferred examples of such diseases are cancer, as demonstrated herein for lung cancer. The ratios of gene expression also can be used to predict a condition outcome or condition prognosis, to monitor onset of a condition, to monitor treatment, and to select a course of treatment for a condition.

Genes to be used for ratio analysis need only have statistically significant differences in means although additional filtering criteria can be applied as necessary to produce a more refined list of genes. These additional criteria are well known to those of ordinary skill in the art. For example, in preferred embodiments, requiring at least a 2-fold difference in means is a common and widely used threshold for considering genes to be truly differentially expressed to take into account inherent biological variability. Preferably, requiring that at least one mean be greater than a specific threshold value ensures that at least one gene will be expressed above the inherent "noise" (i.e., variability) of the device used to measure gene expression levels. This last criterion is recognized by those of ordinary skill in the art as a critical aspect of measuring gene expression using any device and is routinely applied in some form or another. Since the threshold value is experiment and device specific, it will need to be empirically determined in each instance.

Different cancers or different gene sets may have different ratios or threshold values that are useful as predictors of prognosis or outcome. It will be quite clear to the skilled person, based on the knowledge in the art, that different sets of genes as expressed in different cancers may generate different ratios. The threshold may be subject to optimization on a case-by-case basis to reflect inherent experimental and technical variability in the measurement of gene expression levels.

In some instances, genes significantly overexpressed in a particular group are correlated with a clinical variable of interest. These correlations will also be reflected in ratio values. For example a decision to treat based on a ratio test might have a different ratio than the ratio that, for example, warrants a treatment change.

The Examples below exemplify this concept for a number of different cancers and gene sets. However, any differences in ratios or threshold numbers do not adversely impact the clarity and definiteness of the claims as presently written.

The gene expression data for calculation of the ratios may be obtained from analysis of biological samples including tissue, blood, urine, cerebrospinal fluid or other bodily fluids of a subject (e.g., humans or other animals). The expression data can be used without any transformation to calculate a simple ratio of two or more genes as exemplified in the Examples, or data transformation can be applied prior to, or as a part of, calculating the ratios.

The ratio calculation and/or data transformation can be performed by the device that captures the expression data (e.g., a device for performing real-time PCR or a microarray reader), or can be performed by a separate computer running appropriate software.

In certain embodiments, software for calculating ratios can be provided on a computer connected by data link to a data generating device, such as a microarray reader or PCR machine. Any standard data link can be used, including serial or parallel cables, radio frequency or infrared telemetry links, LAN connections, WAN connections, etc. Alternatively, data can be transferred by computer-readable medium (e.g., magnetic or optical medium) and read by the software. The data also can be entered directly by the user via user interface, such as a keyboard, monitor, mouse, graphical user interface such as touch screen, etc. The computer may be contained within the data generating device, providing an integrated system for generating raw data, calculating ratios, and displaying such ratios. One or more computers also may be linked to one or more data generating devices and one or more display devices, such as in a local area network or wide area network.

After acquiring the raw gene expression data from the data generating device, the data for the variables examined can be used to calculate gene expression ratios in accordance with the methods of the invention. The software can allow the user to select a number of genes preferred for detection, diagnosis or prognosis, or the software may calculate ratios for a standardized set or sets of genes (e.g., genes known to be useful for classification of a tissue type or set of tissue types). The software can execute data transformation algorithms from a preselected group, or can allow the user to input other algorithms. The ratio data can be stored in a data file, printed, and/or directly displayed to the user on a graphical user interface.

In one embodiment of the invention, a visual display is used to display the ratio data for the detection, classification, diagnosis and or prediction of prognosis. The visual display can be a graphical user interface, such as a monitor, or a printer.

The invention also relates to the identification of a set of genes that permit confirmation of the presence of abnormal cells (e.g., cancer cells) in biological samples. For example, probes for the expression of the genes can be incorporated into a custom array for detection, diagnosis, and classification cancer (e.g., lung cancer). The genes identified permit, inter alia, rapid screening of cancer samples by nucleic acid microarray hybridization or protein expression technology to determine the expression of the specific genes and thereby to predict the outcome of the cancer. A microarray also can be used to detect, diagnose, and differentiate among cancers from lung cancer (e.g., adenocarcinoma, squamous carcinoma, large cell carcinoma, and small cell lung cancer), normal lung tissue and/or pleura. Such screening is beneficial, for example, in selecting the course of treatment to provide to the cancer patient (i.e., directing therapy), and to monitor the efficacy of a treatment.

The invention differs from traditional diagnostic and classification techniques with respect to the speed, simplicity, and reproducibility of the diagnostic assay. The invention also differs from other microarray-based diagnostic methods in that it does not require extensive data analysis or data transformation employing complex algorithms. Further, the invention differs from other diagnostic methods in that it permits accurate diagnosis and classification of conditions (e.g., cancer, such as lung cancer) by the analysis of a limited set of genes. The use of a limited set of genes in the methods permits the use of simpler methods for acquisition of data, e.g., nucleic acid hybridization based methods such as RT-PCR, that do not generate massive quantities of data from parallel analysis of a large number of genes. The invention also presents targets for drug development because it identifies genes that are differentially expressed in conditions (e.g., tumors and cancers), which can be utilized in the development of drugs to treat such conditions, e.g., by reducing expression of the genes or reducing activity of proteins encoded by the genes.

The invention simplifies prognosis determination by providing an identified set of a small number of genes whose level of expression in lung cancer predicts clinical outcome as defined by, e.g., patient survival times. In developing the invention, RNA expression phenotyping was performed using high density microarrays generated from quantitative expression data on over 12,000 genes, which have been analyzed to identify specific probe sets (genes). The expression gene set has multifold uses including, but not limited to, the following examples. The expression gene set may be used as a prognostic tool for lung cancer, to make possible more finely tuned diagnosis of multiple types of lung cancer and allow healthcare professionals to tailor treatment to individual patients' needs. The invention can also assess the efficacy of cancer treatment by determining progression or regression of the lung cancer in patients before, during, and after treatment. Another utility of the expression gene set is in the biotechnology and pharmaceutical industries' research on disease pathway discovery for therapeutic targeting. The invention can identify alterations in gene expression in different types of lung cancer and can also be used to uncover and test candidate pharmaceutical agents to treat lung cancer.

As used herein, a subject is a human, non-human primate, cow, horse, pig, sheep, goat, dog, cat, or rodent. In all embodiments human subjects are preferred. In aspects of the invention pertaining to diagnosis of lung cancer, the subject is a human either suspected of having lung cancer or having been diagnosed with lung cancer. In aspects of the invention pertaining to cancer diagnosis in general, using the non-linear methods employing ratios of gene expression described herein, the subject preferably is a human suspected of having cancer, or a human having been previously diagnosed as having cancer.

Methods for identifying subjects suspected of having a condition (e.g., cancer) may include physical examination, subject's family medical history, subject's medical history (such as lung cancer), biopsy, or a number of imaging technologies such as ultrasonography, computed tomography, magnetic resonance imaging, magnetic resonance spectroscopy, or positron emission tomography. Diagnostic methods for cancer (e.g., such as lung cancer) and the clinical delineation and diagnosis of conditions (e.g., cancer, such as lung cancer) are well known to those of skill in the medical arts.

As used herein, a tissue sample is tissue obtained from a tissue biopsy using methods well known to those of ordinary skill in the related medical arts. Methods for obtaining the sample from the biopsy include gross apportioning of a mass, microdissection, laser-based microdissection, or other art-known cell-separation methods. The phrase "suspected of being cancerous" as used herein means a cancer tissue sample believed by one of ordinary skill in the medical arts to contain cancerous cells.

Because of the variability of the cell types in diseased-tissue biopsy material, and the variability in sensitivity of the diagnostic methods used, the sample size required for analysis may range from 1, 10, 50, 100, 200, 300, 500, 1000, 5000, 10,000, to 50,000 or more cells. The appropriate sample size may be determined based on the cellular composition and condition of the biopsy and the standard preparative steps for this determination and subsequent isolation of the nucleic acid for use in the invention are well known to one of ordinary skill in the art. An example of this, although not intended to be limiting, is that in some instances a sample from the biopsy may be sufficient for assessment of RNA expression without amplification, but in other instances the lack of suitable cells in a small biopsy region may require use of RNA conversion and/or amplification methods or other methods to enhance resolution of the nucleic acid molecules. Such methods, which allow use of limited biopsy materials, are well known to those of ordinary skill in the art and include, but are not limited to: direct RNA amplification, reverse transcription of RNA to cDNA, amplification of cDNA, or the generation of radio-labeled nucleic acids.

As used herein, the phrase determining the expression of a set of nucleic acid molecules in the tissue means identifying RNA transcripts in the tissue sample by analysis of nucleic acid or protein expression in the tissue sample. As used herein for diagnosis of lung cancer or the type of lung cancer and/or determination of outcome of lung cancer patients, "set" refers to a group of nucleic acid molecules that include one or more, preferably 2, 3, 4, 5, 6, 7, 8, 9, 10, 11, 12, 13, 14, 15, 16, 17, 18, 19, 20, 21, 22, 23, 24, 25, 26, 27, 28, 29, 30 or more different nucleic acid sequences from the group of nucleic acid sequences in the Examples. Other sets will be used for other conditions to determine gene ratios for diagnosis, outcome determination and the like; some of these data sets are described in the Examples below.

The expression of the set of nucleic acid molecules in the sample from the patient suspected of having lung cancer can be compared to the expression of the set of nucleic acid molecules in a sample of tissue that is non-cancerous. As used herein with respect to diagnosis of lung cancer, non-cancerous tissue means tissue determined by one of ordinary skill in the medical art to have no evidence of lung cancer based on standard diagnostic methods including, but not limited to, histologic staining and microscopic analysis.

Nucleic acid markers for a condition (e.g., cancer, such as lung cancer) are nucleic acid molecules that by their presence or absence indicate the presence of absence of the condition (e.g., cancer, such as lung cancer). In tissue, certain nucleic acid molecules are expressed at different levels depending on whether tissue is diseased or not.

Hybridization methods for nucleic acids are well known to those of ordinary skill in the art (see, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York). The nucleic acid molecules from a lung cancer tissue sample hybridize under stringent conditions to nucleic acid markers expressed in the lung cancer. In one embodiment the markers are sets of two or more of the nucleic acid molecules as set forth in the Examples.

The lung cancer nucleic acid markers disclosed herein are known genes and fragments thereof. It may be desirable to identify variants of those genes, such as allelic variants or single nucleotide polymorphisms (SNPs) in tissues. Accordingly, methods for identifying lung cancer nucleic acid markers, including variants of the disclosed full-length cDNAs, genomic DNAs, and SNPs are also included in the invention. The methods include contacting a nucleic acid sample (such as a cDNA library, genomic library, genomic DNA isolate, etc.) with a nucleic acid probe or primer derived from one of the nucleic acid molecules as set forth in the Examples. The nucleic acid sample and the probe or primer hybridize to complementary nucleotide sequences of nucleic acids in the sample, if any are present, allowing detection of nucleic acids related to the nucleic acid molecules as set forth in the Examples. Preferably the probe or primer is detectably labeled. The specific conditions, reagents, and the like can be selected by one of ordinary skill in the art to selectively identify nucleic acids related to sets of two or more of the nucleic acid molecules as set forth in the Examples. The isolated nucleic acid molecule can be sequenced according to standard procedures.

In addition to native nucleic acid markers (i.e., the nucleic acid molecules set forth in the Examples), the invention also includes degenerate nucleic acids that include alternative codons to those present in the native materials. For example, serine residues are encoded by the codons TCA, AGT, TCC, TCG, TCT, and AGC. Each of the six-codons is equivalent for the purposes of encoding a serine residue. Similarly, nucleotide sequence triplets that encode other amino acid residues include, but are not limited to: CCA, CCC, CCG, and CCT (proline codons); CGA, CGC, CGG, CGT, AGA, and AGG (arginine codons); ACA, ACC, ACG, and ACT (thronine codons); AAC and AAT (asparagine codons); and ATA, ATC, and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides modified nucleic acid molecules, which include additions, substitutions, and deletions of one or more nucleotides such as the allelic variants and SNPs described above. In preferred embodiments, these modified nucleic acid molecules and/or the polypeptides they encode retain at least one activity or function of the unmodified nucleic acid molecule and/or the polypeptides, such as hybridization, antibody binding, etc. In certain embodiments, the modified nucleic acid molecules encode modified polypeptides, preferably polypeptides having conservative amino acid substitutions. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules that encode polypeptides having single amino acid changes can be prepared for use in the methods and products disclosed herein. Each of these nucleic acid molecules can have one, two, or three nucleotide substitutions exclusive of nucleotide changes corresponding to the degeneracy of the genetic code as described herein. Likewise, modified nucleic acid molecules that encode polypeptides having two amino acid changes can be prepared, which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions that code for the amino acid substitutions. Additional nucleic acid molecules that encode polypeptides having additional substitutions (i.e., 3 or more), additions or deletions [e.g., by introduction of a stop codon or a splice site(s)] also can be prepared and are embraced by the invention as readily envisioned by one of ordinary skill in the art. Any of the foregoing nucleic acids can be tested by routine experimentation for retention of structural relation to or activity similar to the nucleic acids disclosed herein.

In the invention, standard hybridization techniques of microarray technology are utilized to assess patterns of nucleic acid expression and identify nucleic acid marker expression. Microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

In one of the preferred embodiments, the MetriGenix Flow-thru Chip® (FTC) is utilized to assess nucleic acid expression and profiling. MetriGenix Flow-thru Chip® is a microarray device for bioanalytical analysis in which molecular interactions occur within a three-dimensional matrix of microchannels. Microchannels connect the upper and lower faces of the device such that fluid can flow through them. One important embodiment of the MetriGenix Flow-thru Chip® that may be utilized in the instant invention is the MGX-8 Multi-analyte System which is an automated microarray platform that performs biomolecular assays for nucleic acid or protein targets. The system processes Flow-thru Chips® (FTC) called TipChips™ that are moved between wells containing the target solutions and assay reagents.

According to the present invention, microarray substrates may include but are not limited to glass, silica, aluminosilicates, borosilicates, metal oxides such as alumina and nickel oxide, various clays, nitrocellulose, or nylon. In all embodiments a glass substrate is preferred. According to the invention, probes are selected from the group of nucleic acids including, but not limited to: DNA, genomic DNA, cDNA, and oligonucleotides; and may be natural or synthetic. Oligonucleotide probes preferably are 20 to 25-mer oligonucleotides and DNA/cDNA probes preferably are 500 to 5000 bases in length, although other lengths may be used. Appropriate probe length may be determined by one of ordinary skill in the art by following art-known procedures. In one embodiment, preferred probes are sets of two or more of the nucleic acid molecules set forth in the Examples. Probes may be purified to remove contaminants using standard methods known to those of ordinary skill in the art such as gel filtration or precipitation.

In one embodiment, the microarray substrate may be coated with a compound to enhance synthesis of the probe on the substrate. Such compounds include, but are not limited to, oligoethylene glycols. In another embodiment, coupling agents or groups on the substrate can be used to covalently link the first nucleotide or oligonucleotide to the substrate. These agents or groups may include, but are not limited to: amino, hydroxy, bromo, and carboxy groups. These reactive groups are preferably attached to the substrate through a hydrocarbyl radical such as an alkylene or phenylene divalent radical, one valence position occupied by the chain bonding and the remaining attached to the reactive groups. These hydrocarbyl groups may contain up to about ten carbon atoms, preferably up to about six carbon atoms. Alkylene radicals are usually preferred containing two to four carbon atoms in the principal chain. These and additional details of the process are disclosed, for example, in U.S. Pat. No. 4,458,066, which is incorporated by reference in its entirety.

In one embodiment, probes are synthesized directly on the substrate in a predetermined grid pattern using methods such as light-directed chemical synthesis, photochemical deprotection, or delivery of nucleotide precursors to the substrate and subsequent probe production.

In another embodiment, the substrate may be coated with a compound to enhance binding of the probe to the substrate. Such compounds include, but are not limited to: polylysine, amino silanes, amino-reactive silanes (*The Chipping Forecast*, Nature Genetics, Vol. 21, January 1999,) or chromium (Gwynne and Page, Science, Aug. 6, 1999). In this embodiment, presynthesized probes are applied to the substrate in a precise, predetermined volume and grid pattern, utilizing a computer-controlled robot to apply probe to the substrate in a contact-printing manner or in a non-contact manner such as ink jet or piezo-electric delivery. Probes may be covalently linked to the substrate with methods that include, but are not limited to, UV-irradiation. In another embodiment probes are linked to the substrate with heat.

Targets are nucleic acids selected from the group, including but not limited to: DNA, genomic DNA, cDNA, RNA, mRNA and may be natural or synthetic. In all embodiments, nucleic acid molecules from human tissue are preferred. The tissue may be obtained from a subject or may be grown in culture (e.g., from a lung cancer cell line).

In embodiments of the invention one or more control nucleic acid molecules are attached to the substrate. Preferably, control nucleic acid molecules allow determination of factors including but not limited to: nucleic acid quality and binding characteristics; reagent quality and effectiveness; hybridization success; and analysis thresholds and success. Control nucleic acids may include but are not limited to expression products of genes such as housekeeping genes or fragments thereof.

In one embodiment of the invention, expression of nucleic acid markers is used to select clinical treatment paradigms for the different types of condition (e.g., cancer, such as lung cancer). Treatment options for cancer, as described herein, may include but are not limited to: radiotherapy, chemotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment paradigm based on evaluation of differential expression of sets of two or more genes, such as those set forth in the Examples for the different types of lung cancer. Cancers that express markers that are indicative of a more aggressive cancer or poor prognosis may be treated with more aggressive therapies.

Progression or regression of a condition (e.g., lung cancer) is determined by comparison of two or more different tissue samples (e.g., lung cancer tissue samples) taken at two or more different times from a subject. For example, progression or regression may be evaluated by assessments of expression of sets of two or more of the nucleic acid targets, preferably using ratios of expression, including but not limited to nucleic acid molecules set forth in the Examples, in a lung cancer tissue sample from a subject before, during, and following treatment of the lung cancer. Progression or regression of other cancers or conditions would be determined similarly.

In another embodiment, novel pharmacological agents useful in the treatment of different conditions can be identified by assessing valuations in the expression of two or more nucleic acid markers. For example, different types of lung cancer can be identified by assessing variations in the expression of sets of two or more lung cancer nucleic acid markers (preferably, variations in the ratios of expression), from among nucleic acid molecules set forth in the Examples, prior to and after contacting lung cancer cells or tissues with candidate pharmacological agents for the treatment of lung cancer. The cells may be grown in culture (e.g. from a lung cancer cell line), or may be obtained from a subject, (e.g., in a clinical trial of candidate pharmaceutical agents to treat a lung cancer). Alterations in expression of two or more sets of nucleic acid markers, from among nucleic acid molecules set forth in the Examples, in lung cancer cells or tissues tested before and after contact with a candidate pharmacological agent to treat the lung cancer, indicate progression, regression, or stasis of the lung cancer thereby indicating efficacy of candidate agents and concomitant identification of lead compounds for therapeutic use in the lung cancer.

The invention further provides efficient methods of identifying pharmacological agents or lead compounds for agents active at the cellular function of the condition. Generally, the screening methods involve assaying for compounds that beneficially alter condition (e.g., lung cancer) nucleic acid molecule expression. Such methods are adaptable to automated, high-throughput screening of compounds.

The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, the candidate agent (e.g., anti-lung cancer candidate agent) specifically binds the cellular binding target, a portion thereof or analog thereof. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the candidate agent (e.g., anti-lung cancer candidate agent) and one or more binding targets is detected by any convenient method available to the user. For cell-free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal-to-noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of the candidate agent (e.g., anti-cancer agent) binding to a target molecule typically encodes a directly or indirectly detectable product, e.g., β-galactosidase activity, luciferase activity, and the like. For cell-free binding assays, one of the components usually comprises, or is coupled to, a detectable label. A wide variety of labels can be used, such as those that provide direct detection (e.g., radioactivity, luminescence, optical, or electron density, etc) or indirect detection (e.g., epitope tag such as the FLAG epitope, enzyme tag such as horseradish peroxidase, etc.). The label may be bound to a candidate agent (e.g., an anti-cancer agent) binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention thus generally provides gene (e.g., lung cancer gene) or protein-specific binding agents, methods of identifying and making such agents, and their use in diagnosis, therapy and pharmaceutical development. For example, lung cancer gene- or protein-specific pharmacological agents are useful in a variety of diagnostic and therapeutic applications as described herein. In general, the specificity of a gene (e.g., lung cancer gene) or protein binding to a binding agent is shown by binding equilibrium constants. Targets that are capable of selectively binding a gene (e.g., lung cancer gene) preferably have binding equilibrium constants of at least about $10^7$ $M^{-1}$, more preferably at least about $10^8$ $M^{-1}$, and most preferably at least about $10^9$ $M^{-1}$. The wide variety of cell-based and cell-free assays may be used to demonstrate gene (e.g., lung cancer gene) gene-specific binding. Cell-based assays include one, two and three hybrid screens, assays in which cancer gene-mediated transcription is inhibited or increased, etc. Cell-free assays include gene (e.g., lung cancer gene) gene-protein binding assays, immunoassays, etc. Other assays useful for screening agents which bind polypeptides (e.g., lung cancer polypeptides) include fluorescence resonance energy transfer (FRET), and electrophoretic mobility shift analysis (EMSA).

In another aspect of the invention, pre- and post-treatment alterations in expression of two or more sets of nucleic acid markers, for example lung cancer nucleic acid markers including, but not limited to, nucleic acid molecules set forth in the Examples, in cells or tissues may be used to assess treatment parameters including, but not limited to: dosage, method of administration, timing of administration, and combination with other treatments as described herein.

Expression of cancer nucleic acid molecules can also be determined using protein measurement methods, e.g., for use in the ratio-based diagnostic and prognostic methods described herein. For example, the expression of lung cancer genes such as nucleic acid molecules set forth in the Examples, can be determined by examining the expression of polypeptides encoded by nucleic acid molecules set forth in the Examples. Preferred methods of specifically and quantitatively measuring proteins include, but are not limited to: mass spectroscopy-based methods such as surface enhanced laser desorption ionization (SELDI; e.g., Ciphergen Protein-Chip System), non-mass spectroscopy-based methods, immunoassay methods such as ELISA and immunohistochemistry-based methods such as 2-dimensional gel electrophoresis.

SELDI methodology may, through procedures known to those of ordinary skill in the art, be used to vaporize microscopic amounts of protein and to create a "fingerprint" of individual proteins, thereby allowing simultaneous measurement of the abundance of many proteins in a single sample. Preferably SELDI-based assays may be utilized to classify conditions (e.g., cancer, such as lung cancer). Such assays preferably include, but are not limited to the following examples. Gene products discovered by RNA microarrays may be selectively measured by specific (antibody mediated) capture to the SELDI protein disc (e.g., selective SELDI). Gene products discovered by protein screening (e.g., with 2-D gels), may be resolved by "total protein SELDI" optimized to visualize those particular markers of interest from among polypeptides encoded by nucleic acid molecules set forth in the Examples. Predictive models of tumor classification from SELDI measurement of multiple markers from among polypeptides encoded by nucleic acid molecules set forth in the Examples may be utilized for the SELDI strategies.

The invention further includes protein microarrays for analyzing expression of polypeptides associated with certain conditions (e.g., lung cancer-associated polypeptides selected from those encoded by nucleic acid molecules set forth in the Examples). In this aspect of the invention, standard techniques of microarray technology are utilized to assess expression of the polypeptides associated with certain conditions (e.g., lung cancer-associated polypeptides) and/or identify biological constituents that bind such polypeptides. The constituents of biological samples include antibodies, lymphocytes particularly T lymphocytes), and the like. Protein microarray technology, which is also known by other names including: protein chip technology and solid-phase protein array technology, is well known to those of ordinary skill in the art and is based on, but not limited to, obtaining an array of identified peptides or proteins on a fixed substrate, binding target molecules or biological constituents to the peptides, and evaluating such binding. See, e.g., G. MacBeath and S. L. Schreiber, "Printing Proteins as Microarrays for High-Throughput Function Determination," Science 289 (5485):1760-1763, 2000.

Preferably antibodies or antigen binding fragments thereof that specifically bind polypeptides selected from the group consisting of those encoded by nucleic acid molecules such as, for example, those set forth in the Examples are attached to the microarray substrate in accordance with standard attachment methods known in the art. These arrays can be used to quantify the expression of the polypeptides identified herein.

In some embodiments of the invention, one or more control peptide or protein molecules are attached to the substrate. Preferably, control peptide or protein molecules allow determination of factors such as peptide or protein quality and binding characteristics, is reagent quality and effectiveness, hybridization success, and analysis thresholds and success.

The use of such methods to determine expression of, for example, lung cancer nucleic acids from among nucleic acid molecules set forth in the Examples and/or proteins encoded by nucleic acid molecules set forth in the Examples can be done with routine methods known to those of ordinary skill in the art and the expression determined by protein measurement methods may be used as a prognostic method for selecting treatment strategies for lung cancer patients.

The present invention is not limited in scope by the Examples provided, since the Examples are intended as illustrations of various aspects of the invention and other functionally equivalent embodiments are within the scope of the invention. Various modifications of the invention in addition to those shown are described herein will become apparent to those skilled in the art for the foregoing description and fall within the scope of the appended claims. The advantages and objects of the invention are not necessarily encompassed by each embodiment of the invention.

All references, patents, and patent publications that are recited in this application are incorporated in their entirety herein by reference.

EXAMPLES

Example 1

Introduction

Lung cancer is one of the most common cancers in the Western world and the number one cause of cancer deaths for both men and women in the United States. Up to 80% of lung cancer patients have non-small cell lung cancer (NSCLC), a histological category of primary lung cancer that includes adenocarcinoma (ADCA), squamous cell carcinoma (SCC) and large cell carcinoma. The majority of the remainder have small cell lung cancer (SCLC). Other types of primary lung malignancies include pulmonary carcinoid (1% of all primary lung malignancies).[1,2]

The majority of patients with lung cancer usually present with advanced disease pot amenable to surgical therapy. However, screening with spiral computerized tomography (CT) for lung cancer is a technique rapidly gaining popularity in the US with the goal of identifying lung cancer at early stages when it is far more likely to be curable with surgery.[3] Initial studies of this new screening technology demonstrate a high incidence of non-malignant nodules in the lungs of former smokers. The preliminary recommendations are to measure radiographic volume change of all sub-centimeter nodules at three months intervals and obtain biopsy of any growing nodule. In addition, it is recommended to obtain a biopsy of any non-calcified nodule larger than 1 cm for definitive diagnosis.[3-6] Biopsies can be accomplished surgically with Video Assisted Thoracoscopic Surgery (VATS) or via a trans-thoracic fine needle aspiration (FNA).

Percutaneous CT-guided trans-thoracic FNA of lung nodules is a safe and well-accepted cytopathological diagnostic technique that has been applied to lesions as small as 5 mm. There are very few false positive cytological diagnoses, but the false negative rate has been reported to approach 30%.[7] The ability of a cytologist to make a correct diagnosis depends on the quality of cells obtained and the preservation of tissue architecture. Cytological diagnosis by FNA is also hindered by the frequent inability of the cytologist to determine the type of cancer found in the pulmonary nodule and to differentiate metastatic cancer to the lung from primary lung cancer.[8] As a consequence, the clinical diagnostic strategy in the management of many newly discovered pulmonary nodules is to surgically remove those nodules for which a definitive benign histology has not been obtained, or to monitor the size of small (sub-entimeter) nodules with interval CT scans and remove them surgically if they grow[9].

We have recently described a method for translating gene expression profiling data into clinically relevant tests using ratios of gene expression in multiple cancers.[13-17] Here we report the discovery of differentially expressed genes among normal lung and different types of lung cancer. We then used these genes in the development of a gene ratio method for the differential diagnosis of lung cancer/pulmonary nodule. Finally, we provide evidence suggesting that this technique may complement ongoing lung cancer screening strategies through the analysis of FNA samples.

Methods:

Solid tumor and FNA samples: Solid samples and ex vivo FNAs were collected from 15 consecutive patients undergoing lung resection for cancer at Brigham and Women's Hospital. As soon as the specimen was surgically removed from the patient, it was taken to the frozen section room where under the supervision of the pathologist, FNA was obtained through the surrounding pulmonary parenchyma from the palpable nodule and separated from adjacent uninvolved lung using equipment and protocols identical to those currently employed by cytopathologists at our institution (e.g., 3 cc syringe and 22 gauge needle 1.5 inches long). Aspirated FNA material was immediately placed in RNA extraction buffer (Trizol reagent, Invitrogen Life Technologies, Carlsbad, Calif.) for processing. The diagnostic "gold standard" was obtained after pathological analysis of the solid tumor sample. Studies utilizing human tissues were approved by and conducted in accordance with the policies of the Institutional Review Board at Brigham and Women's Hospital.

Gene Expression Profiling Data: Microarray data for normal and tumor tissues was obtained from two sources. Gene expression data for the "training set" of samples (n=145 total) were obtained using Affymetrix high-density oligonucleotide microarrays (U95A chip) with probe sets representing approximately 12,000 genes and consisting of normal lung (n=13), and the following primary tumors: SCLC (n=7), lung ADCA (n=89), lung SCC (n=24), and pulmonary carcinoid (n=12).[18] Gene expression data for all additional primary and metastatic tumor samples (i.e., the "test set") were acquired from a single source using the same Affymetrix U95A microarray.[19] Primary tumors of the test set consisted of lung SCC (n=14), and the following adenocarcinomas: prostate (n=24), colon (n=20), breast (n=25), gastroesophageal (n=12), pancreatic (n=6), and lung (n=13). Metastatic tumors in the test set (n=9) included those arising from breast, colon, prostate, lung, kidney, and ovarian tumors.

Data and Statistical Analysis: To train an expression ratio based predictor model, we used an approach similar to previous published studies.[13-17] We performed 5 separate analyses to determine differences in gene expression patterns between two groups composed of multiple combinations of tissues chosen from the 145 training set samples. In each of the five training subsets, one group was composed of all available samples of a single tissue type and the other group consisted of a random sampling of all remaining tissue types with equal representation based on the remaining tissue type with the smallest number of samples. For example, the lung ADCA training subset (n=117 total) examined differences in gene expression between two groups: "lung ADCA" (n=89) and "not lung ADCA" (n=28 consisting of 7 samples each of the other four tissue types based on the total number of SCLC tissues). This process was repeated sequentially for the remaining training subsets: SCLC (n=55 total), normal lung (n=41 total), lung SCC (n=72 total), and pulmonary carcinoid (n=64 total). This experimental design resulted in 5 training sets with unique sample numbers (and membership) and was used in order to discover optimal discriminating genes in an unbiased fashion while ensuring equal representation among multiple tissue types.

The selection of predictor genes for use in expression ratio-based diagnosis was performed essentially as described[15, 16] with minor modifications. Using a two-sided Student's (parametric) t-test, we identified statistically significant (see Table 1 for exact P values) genes with inversely correlated average expression levels between both groups in each of the 5 training subsets. We then filtered the resulting gene lists to find those genes with a $\geq$2-fold difference in average expression levels between groups. To minimize the effects of background noise, the list of distinguishing genes was additionally refined by requiring that the mean expression level (i.e., Affymetrix "average difference") be >500 in at least one of the two groups, similar to previous studies.[15, 16] A large number of genes were found to fit the filtering criteria in each of the training subsets. To further pare the number of genes, we randomly chose for additional study a total of 8 genes from the among the most statistically significant differentially expressed genes in each training subset. Four of these genes were expressed at relatively higher levels in a single tissue type and 4 were expressed at relatively higher levels in the remaining tissue types combined. There was a single exception: in the "normal lung" training subset, only 3 genes were expressed at relatively higher levels in all non-normal tissues. In one training subset (lung SCC) there was a single case of duplication among the genes chosen for further analysis considering that (i) we randomly chose additional genes for study, (ii) we initially identified genes based strictly on their unique Affymetrix probe set identifiers (and not gene name), and (iii) the same gene can be represented by multiple Affymetrix probe sets.

All possible non-redundant gene-pair expression ratios were separately calculated for each sample in all 5 training subsets by placing single genes overexpressed in each tissue type in the numerator and single genes overexpressed in the combination of all other tissues in the denominator. All negative Affymetrix "average difference" values (i.e., undetectable) were arbitrarily assigned an expression level=1 to facilitate meaningful comparisons. The identity of samples used to generate the gene lists was then predicted in a binary manner using ratio values and a threshold equal to 1. For example, in the lung adenocarcinoma analysis, individual samples with ratio values >1 and <1 were predicted to be "lung ADCA" and "not lung ADCA", respectively. A final diagnostic call was made based on the value of the geometric mean of the 3 most accurately predictive individual ratios using the same criteria Data from two or more highly accurate gene expression ratios were combined by calculating the geometric mean, $(R_1 R_2 R_3 \ldots R_n)^{1/n}$, where R represents a single ratio value. This is the mathematical equivalent to the average of $[\log_2(R_1), \log_2(R_2), \log_2(R_3), \ldots \log_2(R_n)]$. Using the geometric mean value for multiple ratios has the effect of giving equal weight to ratio fold-changes of identical magnitude but opposite direction on the log scale. Finally, all 5 tissue-specific 3-ratio tests were used to comprehensively analyze the 145 samples training set samples. We hypothesized that the identity of any given sample would be the tissue with the greatest geometric mean. No-calls were conservatively made when no tissue-specific geometric mean was >1. In these cases, a diagnosis was attempted using a "majority rules" voting approach's by considering only the direction (and not the magnitude) of all 15 individual tissue ratios relative to the threshold value. The test set of samples was analyzed in exactly the same manner using identical Affymetrix probe-set identifiers. The classification accuracy of the model in a subset of the test set and in FNA samples was assessed using an exact one-sample binomial test. The P-values are reported under the null hypothesis of differential diagnosis randomly assigned with equal probability of 0.5 based on one-sided tests in order to reject lower levels of accuracy. The 95% confidence interval (C.I.) for proportions is based on the exact binomial distribution. All calculations and statistical comparisons were generated using S-PLUS[20], except the exact binomial procedures that were computed using Stata 7 (StataCorp, College Station, Tex.).

Real-time quantitative RT-PCR: Real-time quantitative RT-PCR was performed as described used 2 µg of total RNA.[16] Primer sequences (synthesized by Invitrogen Life Technologies) used for RT-PCR were as follows (forward and reverse, respectively):

```
M4FAP4
(5'-ACTTCTCCATCTCCCCGAAC-3'
and

5'-TGGTAGGACAGGGAGTCACC-3'),

PRDX2
(5'-AGACAATGGAATGGCAGCTT-3'
and

5'-TGCCCAGAAGTGGCATTAGT-3'),

AGER
(5'-TCCACTGGATGAAGGATGGT-3'
and

5'-CAGCTGTAGGTTCCCTGGTC-3')
and

SSR4
(5'-GGAGCAGGATGCGTATAGGA-3'
and

5'-TCTGACTGCACAGATTCTTGG-3').
```

Results:
Identification of predictor genes and generation of a model for the differential diagnosis of lung nodules using gene expression ratios: We discovered a total of 39 predictor genes that fit the filtering criteria and were chosen for further analysis (Table 1). We calculated and assessed for classification accuracy a total of 16 possible individual gene pair ratios for all training subsets except "normal lung". We calculated 12 possible gene pair ratios for his subset since only 3 genes (not 4) were expressed at relatively higher levels in all non-normal tissues. We have previously shown that optimal classification accuracy using expression ratio-based methods can be achieved in most circumstances by combining the expression data from the 3 most accurate individual gene pair ratios.[15,16] Therefore, we obtained a combined score (i.e. geometric mean, see Methods) for each of the training subset samples using the 3 most accurate ratios from each training subset. We found that we could identify these samples with very high accuracy (Table 2).

To systematically and comprehensively analyze the entire cohort of training set samples in parallel, we next calculated all 15 ratios (from Table 2) for every training set sample (n=45 total) and predicted a tissue type according to the criteria stated in the Methods. Not surprisingly, we discovered that expression ratio diagnosis using these 23 genes was highly accurate: 90% (130/145, 95% C.I. 84-94%, $P<10^{-6}$) of the samples were correctly predicted with 5 errors and 10 no-calls. The no-calls included ADCA (n=6), pulmonary carcinoid (n=1), and SCC (n=3). Importantly, no tumors were called "normal". Of the 13 initial no-calls, 3 were resolved on further analysis (as described in the Methods section) and 10 samples remained without definitive diagnosis. The 10 final "no-call" samples had very low, or more frequently undetectable, expression levels for multiple genes used in the analysis and likely reflects microarray defects and/or artifacts related to sample preparation. Interestingly, we found that 12% (17/145) of samples had multiple (n=2 in all cases) combined scores >1. Of these, 88% (15/17) were called correctly with an average 7-fold difference between both combined scores (range=1.3-46.8) with the larger of the two combined scores used to assign a diagnosis.

Verification of expression level ratios as a diagnostic tool: Next we tested the ability of these 5 highly accurate expression ratio combinations to diagnose cancer in a separate cohort of 113 primary tumors and 9 metastatic tumors (i.e., the test set) for which expression profiling data was available.[19] A total of 26 samples (n=13 each of primary lung ADCA and lung SCC) were directly relevant to the validation of the model developed above since they were obtained from primary lung lesions. The remaining tumors were adenocarcinomas originating from tissues other than lung and/or metastatic disease and we used these samples to test multiple hypotheses. We first hypothesized that adenocarcinomas of diverse origin are more similar to one another than to any of the other 4 tissue types examined in this study with respect to global gene expression patterns, and specifically the 23 genes used in the expression ratio diagnostic model. We also hypothesized that the diagnostic model developed herein would be equally applicable in analyzing metastatic tumors. To perform this analysis, we used the expression values for all 23 diagnostic genes to calculate the 5 most accurate 3-ratio combinations and predicted the identity of all 122 samples using exactly the same criteria as before. In this analysis, the classification accuracy for all adenocarcinomas was evaluated without respect to tissue type of origin. The results for the classification of primary tumors (n=113) are presented in Table 3. Overall, our model was 88% (107/122, 95% C.I. 81-93%, $P<10^{-6}$) accurate in identifying the tumor type of test set samples and was 88% (100/113, 95% C.I. 81-94%, $P<10^{-6}$) and 78% (7/9, 95% C.I. 40-97%, P=0.090) accurate within the subset of primary and metastatic tumors, respectively. Specifically, we found that we could accurately (26/28 or 93%, 95% C.I. 76-99%) and significantly ($-2\times10^{-6}$) predict the identity of primary lung tumors and successfully diagnosed both metastatic lung tumors.

Analysis of ex vivo FNAs: There is ample evidence that material obtained from a is FNA is sufficient for both microarray and (RT-)PCR analysis.[12, 21-24] Therefore, we performed a study to directly test the potential of gene ratios to accurately detect cancer in FNA-derived samples. We used simulated ex vivo FNAs in these initial studies to determine if sample acquisition procedures introduced variability and possibly affected the outcome of the test. Pathological analysis of a portion of the solid specimen classified these 15 nodules as NSCLC (n=6), SCC (n=3), SCLC (n=1), pulmonary carcinoid (n=2), bronchioalveolar carcinoma (n=1), ADCA (nil), and benign fibrosis (n=1). Using quantitative RT-PCR, we obtained gene expression data for the 4 genes comprising the "normal lung versus lung tumor" test (from Table 2) from each FNA. Then, we calculated all three ratios in this test and determined if each individual sample was "normal lung" or "lung tumor" according to the criteria detailed above. We found that ratio-based testing could accurately identify FNA samples ($P=10^{-6}$) from non-malignant specimens (87% specificity, 13/15, 95% C.I. 60-98%) and tumor specimens (100% sensitivity, 14/14, (95% C.I. 81-100%). Importantly, neither of the two misclassified samples were tumor tissues (i.e. false-negatives). Interestingly, one preoperatively suspected tumor FNA sample was predicted to be non-malignant (i.e., "normal lung") by the ratio-based cancer detection test. Upon final pathological review, it was determined that this nodule was in fact a fibrotic mass and not a tumor.

Discussion:

In this study we applied the gene ratio technique[13-17] to the detection and diagnosis of lung cancer using a combined approach consisting of multiple data acquisition platforms and sample sources. The primary strength of this technique is that quantitative RT-PCR can be used to validate the model in additional samples and without further reference to "training samples" whose data was acquired on the same platform. In this way, it becomes possible for other clinical investigators without access to complex bioinformatics tools to reproduce initial findings in a large number of samples worldwide. Here for the first time we extend this technique to the classification of more than two tissue types and provide evidence strongly suggesting that this technique is equally useful in the analysis of FNA-derived material.

Strategies to reduce mortality from lung cancer include the development and implementation of an effective screening system for at-risk populations, e.g. spiral CT. As this technique is being studied it is also being rapidly implemented by physicians, and in many cases on demand by patients willing to bear the cost. Spiral CT of the chest can be excessively sensitive and it is generally estimated that only 10% of nodules detected in the lungs of smokers are actually cancerous.[3, 4, 25] FNA of newly discovered pulmonary nodules is an attractive technique but unfortunately is currently limited by the size of the nodule and the accuracy of cytopathology, specifically in distinguishing between false and true negative results which may account for up to a third of all biopsies.[7] The major problem is that a negative cytology is a negative result in the overwhelming majority of the cases. This is often due to inadequate sampling or lack of sufficient cytologic features to call the sample a tumor.[8]

The gene ratio method can potentially address several of these clinical insufficiencies. For example, it could add a genomic component to the diagnosis which requires only the extraction of very small quantities of tumor RNA (i.e. tissue) thereby facilitating the acquisition of samples that would otherwise not demonstrate cytologically diagnostic tumor cells. Also, in the concept of gene ratio-based analysis a diagnosis of "non-malignant" is actually a positive diagnosis of benign tissue and not necessarily a negative result. In our studies, both misclassified FNA samples were normal lung which is less-than-ideal considering that as its virtue, true FNA cytopathology has a very low false-positive rate. Considering that normal lung tissue was obtained from an area proximal to the suspected tumor on the same patient could indicate that tumor cells have infiltrated the surrounding tissue without it being histologically detectable and/or that lung epithelial cells surrounding the tumor are themselves transformed but have not yet formed a tumor. Alternatively, the misclassification could have resulted due to inherent biological variability reflected in gene expression. Unfortunately, like other similar pilot studies,[12] sufficient material was not available to conduct cytological analyses which may have addressed some of these possibilities.

Our experiments used an ideal scenario (i.e. an "ex vivo FNA") to test the ability of multiple distinguishing genes to accurately classify normal and malignant tissues in the context of a gene expression ratio-based model. Even though the syringe, needle gauge, and biopsy technique were all similar to those typical used by cytopathologists at our institution, prior to implementation this technique will require rigorous testing to take into account additional clinical parameters such as patient movement Considering that the "ex vivo" FNA was acquired through the surrounding pulmonary parenchyma and was still accurate at detecting tumor, we believe that the genes as reported will be suitable for use in actual FNAs. Encouragingly, recent work by other investigators have demonstrated the general feasibility of obtaining RNA from patients using actual trans-thoracic CT guided FNA biopsy material suitable for even stringent applications such as gene expression profiling using microarrays.[12]

The genes used in this study have also been partially validated by another group of investigators who used a single gene pair ratio (RAGE/cyclin-B2) for the detection of lung cancer.[26] We independently found that RAGE (a.k.a AGER) is overexpressed in normal lung relative to tumor and is part of our "normal lung" test (Table 2). We also found that cyclin-B2 was statistically significantly (P=0.013) downregulated in normal lung relative to tumors. However, cyclin-B2 was not among our final list of discriminating genes likely due to fundamentally differences in experimental designs since we examined a broader number of tumor types and utilized multiple genes/ratios.

In conclusion, we have produced evidence strongly suggesting that FNAs are suitable for gene ratio-based detection and diagnosis of lung cancer. This technique may be used as an adjunct and as an extension to current cytopathologic techniques in the evaluation of suspicious lung nodules. Whereas cytopathologists require the preservation of tissue architecture and intact cells for definitive diagnosis, the technique described herein only requires intact tumor RNA. Furthermore, other gene ratio based tests, such as for the prognosis of lung cancer,[14] may also be applicable to the analysis of FNAs to aid in tailoring the best therapy for the patient in whom cancer is detected and diagnosed. This approach allows clinicians to tailor the therapy of individual cancer patients.

REFERENCES

1. Bueno R, Wain S C, Wright C D, Moncure A C, Grillo H C, Mathisen D J. Bronchoplasty in the management of low-grade airway neoplasms and benign bronchial stenoses. *Ann Thorac Surg* 1996; 62(3):824-28.
2. Solaini L, Bagioni P, Prusciano F. Di Francesco F, Poddie D B. Video-assisted thoracic surgery (VATS) lobectomy for typical bronchopulmonary carcinoid tumors. *Surg Endosc* 2000; 14(12):1142-45.
3. Henschke C I, McCauley D I, Yankelevitz D F, Naidich D P, McGuinness G, Miettinen O S, et al. Early lung cancer action project: a summary of the findings on baseline screening. *Oncologist* 2001; 6(2):147-52.
4. Henschke C I, Naidich D P, Yankelevitz D F, McGuinness G, McCauley D I, Smith J P, et al. Early lung cancer action project: initial findings on repeat screenings. *Cancer* 2001; 92(1):153-59.
5. Gorlova O, Kimmel M, Henschke C. Modeling of long-term screening for lung carcinoma. *Cancer* 2001; 92(6):1531-40.
6. Miettinen O, Henschke C. CT screening for lung cancer: coping with nihilistic recommendations. *Radiology* 2001; 221(3):592-96.
7. Calhoun P, Feldman P, Armstrong P. Black W, Pope T, Minor G, et al. The clinical outcome of needle aspirations of the lung when cancer is not diagnosed. *Ann Thorac Surg* 1986; 41:592-96.
8. Silverman J. Inflammatory and neoplastic processes of the lung: differential diagnosis and pitfalls in FNA. *Diagn Cytopathol* 1995; 13(5):448-62.
9. Aberle D, Gamsu G, Henschke C, Naidich D, Swensen S. A consensus statement of the Society of Thoracic Radiology: screening for lung cancer with helical computed tomography. *J Thorac Imaging* 2001; 16(1):65-68.
10. Beer D G, Kardia S L R, Huang C-C, Giordana T J, Levin A M, Misek D E, et al. Gene-expression profiles predict survival of patients with lung adenocarcinoma. *Nat Med* 2002; 8(8):816-24.
11. Garber M E, Troyanskaya O G, Schluens K, Petersen S, Thaesler Z, Pacyna-Gengelbach M, et al., Diversity of gene expression in adenocarcinoma of the lung. *Proc Natl. Acad Sci USA* 2002; 99(2):13784-89.
12. Borczuk A C, Shah L, Pearson G D N, Walter K L, Wang L, Austin J H M, et al. Molecular signatures in biopsy specimens of lung cancer. *Am J Respir Crit Care Med* 2004; 170:167-74.
13. Gordon G J, Rockwell G N, Godfrey P A, Jensen R V, Glickman J N, Yeap B W, et al. Validation of genomics-based prognostic tests in malignant pleural mesothelioma. *Clin Cancer Res* 2005; 11:4406-14.
14. Gordon G J, Richards W G, Sugarbaker D J, Jaklitsch M T, Bueno R. A prognostic test for adenocarcinoma of the lung from gene expression profiling data. *Cancer Epidemiol Biomarkers Prev* 2003; 12:905-10.
15. Gordon G J, Jensen R V, Hsiao L-L, Gullans S R, Blumenstock J E, Ramaswami S, et al. Translation of microarray data into clinically relevant cancer diagnostic tests using gene expression ratios in lung cancer and mesothelioma. *Cancer Res* 2002; 62:4963-67.
16. Gordon G J, Hsiao L-L, Jensen R V, Gullans S R, Blumenstock J E, Richards W G, et al. Using gene expression ratios to predict outcome among patients with mesothelioma. *J Natl Cancer Inst* 2003; 95:598-6059.
17. Bueno R, Loughlin K R, Powell M H, Gordon G J. A diagnostic test for prostate cancer from gene expression profiling data. *J Urol* 2004; 171:903-06.
18. Bhattacharjee A, Richards W G, Staunton J, Li C, Monti S, Vasa P, et al. Classification of human lung carcinomas by mRNA expression profiling reveals distinct adenocarcinoma sub-classes. *Proc Natl Acad Sci USA* 2001; 98:13790-95.
19. Su A I, Welsh J B, Sapinoso L M, Kern S G, Dimitrov P, Lapp H, et al. Molecular classification of human carcinomas by use of gene expression signatures. *Cancer Res* 2001; 61:7388-93.

20. Venables W N, Riley B D. Modern Applied Statistics with S-Plus. New York: Springer, 1997.
21. Crnogorac-Jurcevic T, Efthimiou E, Capelli P, Blaveri E, Baron A, Terris B, et al. Gene expression profiles of pancreatic cancer and stromal desmoplasia. *Oncogene* 2001; 20(50):7437-46.
22. Assersohn L, Gangi L, Zhao Y, Dowsett M, Simon R, Powles T J, et al. The feasibility of using fine needle aspiration from primary breast cancers for cDNA mnicroarray analyses. *Clin Cancer Res* 2002; 8(3):794-801.
23. Dey P, Luthra U K, George S S, Prasad A. C-erbB-2 expression and DNA ploidy in breast cancer on fine-needle aspiration cytology material. *Diagn Cytopathol* 2000; 22(4):261-62.
24. Sotiriou C, Powles T J, Dowsett M, Jazaeri A A, Feldman A L, Assersohn L, et al. Gene expression profiles derived from fine needle aspiration correlate with response to systemic chemotherapy in breast cancer. *Breast Cancer Res* 2002; 4(3):R3.
25. Sagawa M, Saito Y, Sato M, Sugita M, Endo C, Takahashi S, et al. Lung cancer screening—its efficacy and limitations. *Gan To Kagaku Ryoho [Jap J Cancer Chemother]* 2002; 29(11):1894-99.
26. Hofmann H-S, Hansen G, Burdach S, Bartling B, Silber R-E, Simm A. Discrimination of human lung neoplasm from normal lung by two target genes. *Am J Respir Crit Care Med* 2004; 170:516-19.

TABLE 1

Lung nodule diagnostic genes

| GenBank Accession # | P value | Ratio[a] | Description (LocusLink ID) |
|---|---|---|---|
| *Normal lung[b]* | | | |
| L38486 | $6.7 \times 10^{-16}$ | 179 | microfibrillar-associated protein 4 (MFAP4) |
| AI312905 | $1.6 \times 10^{-14}$ | 439 | EST |
| M91211 | $7.8 \times 10^{-14}$ | 15 | advanced glycosylation end product-specific receptor (AGER) |
| D88587 | $2.5 \times 10^{-11}$ | 14 | ficolin (FCN3) |
| J04111 | $4.4 \times 10^{-7}$ | 0.35 | v-jun avian sarcoma virus 17 oncogene homolog (JUN) |
| L19185 | $2.7 \times 10^{-5}$ | 0.34 | peroxiredoxin 2 (PRDX2) |
| Z69043 | $9.5 \times 10^{-5}$ | 0.46 | signal sequence receptor, delta (SSR4) |
| *Lung adenocarcinoma* | | | |
| AB000712 | $2.4 \times 10^{-9}$ | 94 | claudin 4 (CLDN4) |
| AF001294 | $4.0 \times 10^{-9}$ | 3.6 | tumor suppressing subtransferable candidate 3 (TSSC3) |
| J05581 | $1.7 \times 10^{-7}$ | 4.1 | mucin 1, transmembrane (MUC1) |
| M18728 | $3.0 \times 10^{-7}$ | 5.4 | carcinoembryonic antigen-related cell adhesion molecule 6 (CEACAM |
| Z78388 | $7.3 \times 10^{-10}$ | 0.31 | neuronal protein (NP25) |
| M25756 | $1.2 \times 10^{-7}$ | 0.03 | secretogranin II (SCG2) |
| U15979 | $1.4 \times 10^{-7}$ | 0.02 | delta-like homolog, *Drosophila* (DLK1) |
| L07335 | $2.1 \times 10^{-7}$ | 0.22 | sex determining region Y-box 2 (SOX2) |
| *Lung squamous cell carcinoma* | | | |
| M21389 | $8.2 \times 10^{-11}$ | 30 | keratin 5 (KRT5) |
| Y16961 | $1.8 \times 10^{-8}$ | 23 | tumor protein 63 kDa with strong homology to p53 (TP63) |
| *L42611 | $3.9 \times 10^{-8}$ | 18 | keratin 6A (KRT6A) |
| *L42611 | $3.9 \times 10^{-8}$ | 18 | keratin 6A (KRT6A) |
| U97105 | $8.7 \times 10^{-7}$ | 0.37 | dihydropyrimidinase-like 2 (DPYSL2) |
| AF004563 | $1.7 \times 10^{-5}$ | 0.48 | syntaxin binding protein 1 (STXBP1) |
| AF042792 | $8.0 \times 10^{-5}$ | 0.32 | calcium channel, voltage-dependent (CACNA2D2) |
| U43203 | $1.8 \times 10^{-4}$ | 0.26 | thyroid transcription factor 1 (TTTF1) |
| *Small cell lung cancer* | | | |
| D82345 | $1.6 \times 10^{-8}$ | 16 | thymosin, beta (TMSNB) |
| AA203476 | $5.6 \times 10^{-8}$ | 9 | pituitary tumor-transforming 1 (PTTG1) |
| U73379 | $1.1 \times 10^{-7}$ | 17 | ubiqiutin-conjugating enzyme E2C (UBE2C) |
| D00762 | $6.6 \times 10^{-7}$ | 11 | proteasome subunit, alpha type, 3 (PSMA3) |
| L25080 | $8.4 \times 10^{-5}$ | 0.28 | ras homolog gene family, member A (ARHA) |
| X05409 | $8.0 \times 10^{-4}$ | 0.20 | aldehyde dehydrogenase 2 (ALDH2) |
| X59798 | 0.002 | 0.24 | cyclin D1 (CCND1) |
| X04366 | 0.008 | 0.25 | calpain 1 (CAPN1) |
| *Pulmonary carcinoid* | | | |
| L18983 | $1.6 \times 10^{-10}$ | 11 | protein tyrosine phosphatase, receptor type, N (PTPRN) |
| AB014558 | $7.8 \times 10^{-10}$ | 102 | cryptochrome 2, photolyase-like (CRY2) |
| U96750 | $4.6 \times 10^{-7}$ | 350 | ras homolog gene family, member I (ARHI) |
| Y00064 | $5.8 \times 10^{-7}$ | 118 | chromogranin B (CHGB) |
| AA203487 | $5.4 \times 10^{-8}$ | 0.03 | CD68 antigen (CD68) |
| AA631972 | $1.1 \times 10^{-7}$ | 0.01 | natural killer cell transcript 4 (NK4) |
| X67325 | $1.2 \times 10^{-7}$ | 0.15 | interferon, alpha-inducible protein 27 (IFI27) |
| X62744 | $3.5 \times 10^{-7}$ | 0.01 | major histocompatibility complex, class II, DM alpha (HLA-DMA) |

Eight diagnostic genes for each tissue type were chosen for further study. Four genes were expressed at relatively higher levels in a single tissue type and 4 genes were expressed at relatively higher levels in an equal number of all other tissue types combined.
[a]average expression level in a single tissue type/average expression level in all other tissue types combined
[b]only 3 genes (not 4) were overexpressed in all non-normal tissues and fit the filtering criteria
*this gene was represented by multiple probe sets on the expression profiling platform of the training set (see Methods)

TABLE 2

Diagnostic accuracy of 3-ratio combinations in training susubsets

| 3-ratio test[a] | Accuracy |
|---|---|
| Normal Lung | |
| MFAP4\PRDX2, AGER\PRDX2, AGER\SSR4 | 100% (41/41) |
| Lung adenocarcinoma | |
| CLDN4\SOX2, CLDN4\NP25, TSSC3\SOX2 | 89% (104/117) |
| Lung squamous cell carcinoma | |
| KRT5\CACNA2D2, KRT6A\TITF1, KRT6A\STXBP1 | 90% (65/72) |
| Small cell lung cancer | |
| PTTG1\CCND1, PSMA3\ALDH2, TMSNB\ALDH2 | 100% (55/55) |
| Pulmonary carcinoid | |
| PTPRN\NK4, CRY2\CD68, CRY2\HLA-DMA | 98% (63/64) |

The 3 most accurate individual ratios identified in each training subset were combined and used to obtain a diagnostic call for samples contained within each subset.
[a], genes are represented by LocusLink symbols found in Table 1

TABLE 3

Distribution of class predictions for test set samples

| Actual identity of unknown sample[a] | Predicted class[a] | | | | | |
|---|---|---|---|---|---|---|
| | LADCA | LSCC | SCLC | PC | NL | No-call |
| LADCA | 12 | 1 | | | | |
| LSCC | 1 | 12 | | | | |
| PR | 24 | | | | | |
| CO | 19 | 1 | | | | |
| BR | 20 | 1 | | 1 | 3 | |
| GA | 9 | 1 | | 1 | 1 | |
| PA | 4 | 1 | | | 1 | |

The value in each box is the number of primary tumors from the test set (n = 112) predicted with a given identity using the expression ratio-based model developed in the training set of samples.
[a]LADCA, lung adenocarcinoma; LSCC, lung squamous cell carcinoma; SCLC, small cell lung cancer; PC, pulmonary carcinoid; NL, normal lung; PR, prostate adenocarcinomas; CO, colon adenocarcinomas; BR, breast adenocarcinomas; GA, gastroesophageal adenocarcinoma; PA, pancreatic adenocarcinoma.

Example 2

We performed an analysis similar to the one we performed in Example 1 for the detection and diagnosis of adenocarcinoma (ADCA) and squamous cell carcinoma (SCC) of the lung since these tumors comprise the overwhelming majority of pulmonary neoplasms.

Methods:

We created a ratio-based model as in Example 1 (using microarray data for a training set of specimens consisting of normal lung (n=12), lung ADCA (n=89), and lung SCC (n=24). First we defined genes/ratio-based tests for cancer detection (i.e., normal lung vs. either type of lung cancer). Then we defined genes/ratio-based tests for cancer diagnosis (i.e., ADCA vs. SCC). Each of these tests were first evaluated in the training set and then in the same test set used in Example 1. We also tested the following hypotheses: i) that non-ADCA and non-SCC tumors will correctly be classified as "tumor" using the cancer detection test, ii) that ADCAs of non-lung origin will correctly be classified as "tumor" (and "ADCA" specifically) using the cancer detection and diagnosis tests, and iii) that these tests will be similarly amenable to the analysis of material obtained via FNA.

Results:

Cancer Detection: We identified a set of statistically significant genes expressed at relatively higher levels in a reciprocal manner in normal lung and both types of lung cancer (Tables 4 and 5, respectively). Although we have found that most (perhaps all) of these genes would be appropriate for constructing a ratio-based predictor model, we chose for further analysis from among the most statistically significant genes those that would be most amenable to RT-PCR.

We identified a 3-ratio (AGER/GPR56, AGER/SPP1, AGER/DDR1) and 5-ratio (AGER/GPR56, AGER/SPP1, AGER/DDR1, GPCR5A/DDR1, GPCR5A/MGC3077) cancer detection test both of which were 100% accurate in identifying the 125 training set samples. When examined in the non-ADCA/SCC samples for which microarray data was available, the 3-ratio test was 92% (11/12) and 86% (6/7) accurate in identifying pulmonary carcinoid and small cell lung cancer tumors, respectively. The 5-ratio test was 100% accurate in identifying both non-ADCA/SCC tumor types. Both tests were 100% accurate in identifying all tumor types in the test set. Primary tumors of the test set consisted of lung SCC (n=13), and the following adenocarcinomas: prostate (n=24), colon (n=20), breast (n=25), gastroesophageal (n=12), pancreatic (n=6), and lung (n=13). Metastatic tumors in the test set (n=9) included those arising from breast, colon, prostate, lung, and kidney tumors.

Next we examined both cancer detection tests in an independent group of 40 patients undergoing resection for a lung mass (primarily lung ADCA or SCC) at our institution. Of these 40 samples, a total of 5 were non-lung primary ADCA/SCC tumors (i.e., n=2 pulmonary carcinoid, n=3 metastatic tumors from colon and kidney combined). For all patients we had discarded solid surgical specimens and "ex vivo" FNA samples of both tumor and adjacent benign lung. Using quantitative RT-PCR, both tests successfully classified solid tumor specimens (i.e., sensitivity) and benign lung specimens (i.e., specificity): 3-ratio test (92% sensitivity, 95% specificity), 5-ratio test (97% sensitivity, 92% specificity). (All 5 non-lung primary ADCA/SCC tumors were correctly classified).

Cancer Diagnosis We identified a set of statistically significant genes expressed at relatively higher levels in a reciprocal manner in lung ADCA and lung SCC Cables 6 and 7, respectively). As before, most (perhaps all) of these genes would be appropriate for constructing a ratio-based predictor model but we chose for final analysis those that would be most amenable to RT-PCR.

We chose for further analysis two 3-ratio tests that were 96% accurate overall in classifying training set samples: Test 1 (CEACAM6/KRT5, CEACAM6/DSP, FLJ12443/DSP) and Test 2 (MUC1/DSP, CEACAM6/KRT5, FLJ12443/KRT5). Test 1 was 97% and 96% accurate within the lung ADCA (n=89) and lung SCC (n=24) training subsets, respectively. Test 2 was 98% and 92% accurate within the lung ADCA (n=89) and lung SCC (n=24) training subsets, respectively. In the test set, Test 1 was 92% accurate overall (24/26) in classifying primary lung ADCA (n=13) and lung SCC (n=13) samples with one error each in ADCA and SCC. Test 2 correctly classified all 26 primary lung samples (100%, 26126). Additional analyses are in progress.

CONCLUSIONS

The cancer detection and diagnosis tests described above are relevant to the analysis of both primary and metastatic lung ADCA and SCC. In addition, we have presented evidence that this simplified approach can be used to accurately detect cancer in non-lung ADCA/SCC cases (i.e., small cell lung cancer, pulmonary carcinoid). This technique is equally applicable to the analysis of FNA.

TABLE 4

Genes overexpressed in normal lung compared to lung cancer.

| Gene Symbol | GenBank Accession # | P value | Ratio[1] | Description |
|---|---|---|---|---|
| CLDN18 | AI312905 | <1.0E−22 | 120.1 | claudin 18 |
| MFAP4 | L38486 | <1.0E−22 | 79.0 | microfibrillar-associated protein 4 |
| AGER | M91211 | <1.0E−22 | 16.9 | advanced glycosylation end product-specific receptor |
| FCN3 | D88587 | <1.0E−22 | 11.7 | ficolin |
| CLEC3B | X64559 | <1.0E−22 | 9.5 | C-type lectin domain family 3, member B |
| FHL1 | AF063002 | <1.0E−22 | 9.1 | four and a half LIM domains 1 |
| AQP1 | U41518 | <1.0E−22 | 7.6 | aquaporin 1 |
| SPOCK2 | D87465 | <1.0E−22 | 7.0 | sparc/osteonectin |
| CAV1 | AF070648 | <1.0E−22 | 6.7 | caveolin 1, caveolae protein, 22 kDa |
| ALOX5AP | AI806222 | <1.0E−22 | 6.3 | arachidonate 5-lipoxygenase-activating protein |
| PECAM1 | AA100961 | <1.0E−22 | 6.2 | Platelet/endothelial cell adhesion molecule (CD31 antigen) |
| TNXA | U89337 | <1.0E−22 | 5.5 | tenascin XA pseudogene /// tenascin XB |
| DF | M84526 | <1.0E−22 | 5.4 | D component of complement (adipsin) |
| TGFBR2 | D50683 | <1.0E−22 | 5.2 | transforming growth factor, beta receptor II (70/80 kDa) |
| VWF | M10321 | <1.0E−22 | 4.9 | von Willebrand factor |
| EMP2 | U52100 | <1.0E−22 | 4.7 | epithelial membrane protein 2 |
| GPX3 | D00632 | <1.0E−22 | 4.6 | glutathione peroxidase 3 (plasma) |
| SPARCL1 | X86693 | <1.0E−22 | 3.7 | SPARC-like 1 (mast9, hevin) |
| ENG | X72012 | <1.0E−22 | 3.5 | endoglin (Oster-Rendu-Weber syndrome 1) |
| DPYSL2 | U97105 | <1.0E−22 | 3.4 | dihydropyrimidinase-like 2 |
| TGFBR2 | D50683 | <1.0E−22 | 3.3 | transforming growth factor, beta receptor II (70/80 kDa) |
| MACF1 | AB007934 | <1.0E−22 | 3.2 | microtubule-actin crosslinking factor 1 |
| PTRF | AL050224 | <1.0E−22 | 3.2 | polymerase I and transcript release factor |
| KLF9 | D31716 | <1.0E−22 | 3.0 | Kruppel-like factor 9 |
| HEG1 | W52003 | <1.0E−22 | 2.7 | HEG homolog 1 (zebrafish) |
| TACC1 | AF049910 | <1.0E−22 | 2.6 | transforming, acidic colied-coil containing protein 1 |
| STOM | X85116 | <1.0E−22 | 2.1 | stomatin |
| LAMP3 | AB013924 | 1.1E−16 | 4.8 | lysosomal-associated membrane protein 3 |
| PPAP2B | AF017786 | 1.1E−16 | 4.6 | phosphatidic acid phosphatase type 2B |
| HYAL2 | U09577 | 1.1E−16 | 2.2 | hyaluronoglucosaminidase 2 |
| VSIG4 | AL034397 | 3.3E−16 | 2.8 | V-set and immunoglobulin domain containing 4 |
| SPTAN1 | J05243 | 4.4E−16 | 2.1 | spectrin, alpha, non-erythrocytic 1 (alpha-fodrin) |
| SLC39A8 | AL049963 | 8.9E−16 | 4.5 | solute carrier family 39 (zinc transporter), member 8 |
| CLDN5 | AF000959 | 10.0E−16 | 6.1 | claudin 5 |
| PMP22 | D11428 | 6.2E−15 | 2.6 | peripheral myelin protein 22 |
| EMP3 | U87947 | 1.4E−14 | 2.7 | epithelial membrane protein 3 |
| SERPING1 | X54486 | 1.7E−14 | 2.2 | serpin peptidase inhibitor, clade G (C1 inhibitor), member 1 |
| MRC1 | M93221 | 2.3E−14 | 3.9 | mannose receptor, C type 1 |
| ABCA3 | U78735 | 2.9E−14 | 4.8 | ATP-binding cassette, sub-family A (ABC1), member 3 |
| AHNAK | M80899 | 7.3E−14 | 2.5 | AHNAK nucleoprotein (desmoyokin) |
| HLA-E | M16714 | 9.2E−14 | 2.7 | major histocompatibility complex, class I, E |
| CACNA2D2 | AF042792 | 2.8E−13 | 3.3 | calcium channel, voltage-dependent, alpha 2/delta subunit 2 |
| NTE | AJ004832 | 4.2E−13 | 2.8 | neuropathy target esterase |
| RRAS | M14949 | 4.3E−13 | 2.3 | related RAS viral (r-ras) oncogene homolog |
| — | AA156240 | 9.3E−13 | 3.1 | — |
| SFTPD | X65018 | 1.5E−12 | 3.6 | surfactant, pulmonary-associated protein D |
| SCGB1A1 | T92248 | 1.7E−12 | 7.2 | secretoglobin, family 1A, member 1 (uteroglobin) |
| PTGDS | M98539 | 4.0E−12 | 3.5 | prostaglandin D2 synthase 21 kDa (brain) |
| PTGDS | M98539 | 5.5E−12 | 2.8 | prostaglandin D2 synthase 21 kDa (brain) |
| ADH1A | M12963 | 9.0E−12 | 6.3 | alcohol dehydrogenase 1A (class I), alpha polypeptide |
| HLA-DRB4 | U70543 | 1.6E−11 | 2.8 | major histocompatibility complex, class II, DR beta 4 |
| SOD3 | J02947 | 1.7E−11 | 2.3 | superoxide dismutase 3, extracellular |
| GAS6 | L13720 | 2.6E−11 | 2.0 | growth arrest-specific 6 |
| RARRES2 | U77594 | 4.2E−11 | 2.3 | retinoic acid receptor responder (tazarotene induced) 2 |
| PTGDS | M98539 | 5.7E−11 | 6.6 | prostaglandin D2 synthase 21 kDa (brain) |
| FBP1 | U21931 | 6.5E−11 | 3.5 | fructose-1,6-bisphosphatase 1 |
| CYP4B1 | J02871 | 9.4E−11 | 2.0 | cytochrome P450, family 4, subfamily B, polypeptide 1 |
| RAMP3 | AJ001016 | 1.7E−10 | 3.5 | receptor (calcitonin) activity modifying protein 3 |
| KLF6 | U44975 | 2.0E−10 | 2.1 | Kruppel-like factor 6 |
| SEPP1 | Z11793 | 3.4E−10 | 2.4 | selenoprotein P, plasma, 1 |
| C10orf10 | AB022718 | 4.2E−10 | 3.7 | chromosome 10 open reading frame 10 |
| FCGRT | U12255 | 1.1E−09 | 2.1 | Fc fragment of IgG, receptor, transporter, alpha |
| ZYX | X95735 | 1.3E−09 | 2.5 | zyxin |
| HBA1 | J00153 | 1.9E−09 | 5.4 | hemoglobin, alpha 1 /// hemoglobin, alpha 2 |
| TGM2 | M55153 | 2.1E−09 | 2.6 | transglutaminase 2 |
| IL7R | M29696 | 2.7E−09 | 2.6 | Interleukin 7 receptor |
| PRELP | U41344 | 3.6E−09 | 2.1 | proline/arginine-rich end leucine-rich repeat protein |
| CSRP1 | M33146 | 3.9E−09 | 2.2 | cysteine and glycine-rich protein 1 |
| HBB | L48215 | 6.8E−09 | 4.9 | hemoglobin, beta /// hemoglobin, beta |
| — | AB002344 | 7.8E−09 | 2.0 | — |
| TIMP3 | U14394 | 1.3E−08 | 2.0 | TIMP metallopeptidase inhibitor 3 |
| FCGR3A | J04162 | 2.0E−08 | 2.3 | Fc fragment of IgG, low affinity IIIa, receptor (CD16a) |
| C1QB | X03084 | 2.2E−08 | 2.8 | complement component 1 |
| SFTPC | J03553 | 3.2E−08 | 4.5 | surfactant, pulmonary-associated protein C |
| TPSAB1 | M30038 | 4.2E−08 | 3.6 | tryptase alpha/beta 1 |

TABLE 4-continued

Genes overexpressed in normal lung compared to lung cancer.

| Gene Symbol | GenBank Accession # | P value | Ratio[1] | Description |
|---|---|---|---|---|
| MT2A | AI547258 | 7.3E−08 | 2.4 | metallothionein 2A |
| ALDH2 | X05409 | 9.1E−08 | 2.2 | aldehyde dehydrogenase 2 family |
| HBB | M25079 | 9.9E−08 | 6.5 | hemoglobin, beta |
| MT1A | K01383 | 1.5E−07 | 4.7 | metallothionein 1A (functional) |
| — | HG2261-HT2351 | 1.5E−07 | 2.5 | — |
| HLA-DQB1 | M60028 | 1.5E−07 | 2.4 | major histocompatibility complex, class II, DQ beta 1 |
| CD68 | AA203487 | 1.6E−07 | 2.2 | CD68 antigen |
| TIMP3 | U14394 | 2.3E−07 | 2.1 | TIMP metallopeptidase inhibitor 3 |
| GRN | AF055008 | 3.0E−07 | 2.1 | granulin |
| SFTPB | AI820718 | 3.1E−07 | 2.9 | surfactant, pulmonary-associated protein B |
| PPP1R15A | U83981 | 3.3E−07 | 2.3 | protein phosphatase 1, regulatory (inhibitor) subunit 15A |
| GPC3 | U50410 | 4.1E−07 | 3.3 | glypican 3 |
| GPRC5A | AF095448 | 7.5E−07 | 2.6 | G protein-coupled receptor, family C, group 5, member A |
| IL7R | AF043129 | 9.2E−07 | 2.6 | interleukin 7 receptor |
| MT1F | H68340 | 1.3E−06 | 2.5 | metallothionein 1F |
| MYH11 | AF001548 | 1.5E−06 | 3.4 | myosin, heavy polypeptide 11, smooth muscle |
| MT1E | M10942 | 1.8E−06 | 2.2 | metallothionein 1E (functional) |
| MYH11 | AF013570 | 2.1E−06 | 3.5 | myosin, heavy polypeptide 11, smooth muscle |
| NR4A1 | L13740 | 2.1E−06 | 2.9 | nuclear receptor subfamily 4, group A, member 1 |
| DHCR24 | D13643 | 2.2E−06 | 2.2 | 24-dehydrocholesterol reductase |
| MT1H | R93527 | 2.6E−06 | 2.4 | metallothionein 1H |
| S100A4 | W72186 | 3.4E−06 | 2.9 | S100 calcium binding protein A4 |
| TYROBP | W60864 | 4.2E−06 | 2.4 | TYRO protein tyrosine kinase binding protein |
| TSC22D3 | AI635895 | 4.3E−06 | 2.2 | TSC22 domain family, member 3 |
| GPR116 | AB018301 | 5.9E−06 | 2.5 | G protein-coupled receptor 115 |
| HLA-DQA1 | AA868382 | 6.4E−06 | 2.3 | major histocompatibility complex, class II, DQ alpha 1 |
| DUSP1 | X68277 | 8.6E−06 | 2.5 | dual specificity phosphatase 1 |
| CTSH | X16832 | 1.4E−05 | 2.1 | cathepsin H |
| MT1F | M10943 | 1.9E−05 | 2.2 | metallothionein 1F (functional) |
| CRIP1 | AI017574 | 2.5E−05 | 2.0 | cysteine-rich protein 1 (intestinal) |
| SLC2A3 | M20681 | 3.3E−05 | 2.3 | solute carrier family 2 |
| SELENBP1 | U29091 | 3.8E−05 | 2.2 | selenium binding protein 1 |
| IL6 | X04430 | 3.9E−05 | 3.9 | interleukin 6 (interferon, beta 2) |
| DAF | M31516 | 4.3E−05 | 2.0 | decay accelerating factor for complement |
| FOSB | L49169 | 4.4E−05 | 3.2 | FBJ murine osteosarcoma viral oncogene homolog B |
| SFTPB | J02761 | 5.3E−05 | 2.1 | surfactant, pulmonary-associated protein B |
| ZFP36 | M92843 | 8.3E−05 | 2.0 | zinc finger protein 36, C3H type, homolog (mouse) |
| HLA-DRB1 | M16941 | 8.7E−05 | 2.0 | major histocompatibility complex, class II, DR beta 1 |
| CCL2 | M26683 | 1.3E−04 | 2.7 | chemokine (C-C motif) ligand 2 |
| CCL2 | M28225 | 1.5E−04 | 3.1 | chemokine (C-C motif) ligand 2 |
| MYL9 | J02854 | 2.4E−04 | 2.7 | myosin, light polypeptide 9, regulatory |
| SLPI | X04470 | 3.0E−04 | 2.2 | secretory leukocyte peptidase inhibitor |
| NR4A1 | L13740 | 5.3E−04 | 2.1 | nuclear receptor subfamily 4, group A, member 1 |
| CDKN1A | U03106 | 7.4E−04 | 2.1 | cyclin-dependent kinase inhibitor 1A (p21, Cip1) |
| PGC | M18667 | 9.8E−04 | 3.8 | progastricsin (pepsinogen C) |
| CYB5 | L39945 | 1.3E−03 | 2.0 | cytochrome b-5 |

[1]Ratio of average expression level in normal lung samples/average expression level in lung cancer samples per text.

TABLE 5

Genes overexpressed in lung cancer compared to normal lung

| Gene Symbol | GenBank Accession # | P value | Ratio[1] | Description |
|---|---|---|---|---|
| CBX3 | AI797801 | 4.4E−09 | 0.470 | chromobox homolog 3 (HP1 gamma homolog, *Drosophila*) |
| MIF | L19686 | 1.4E−08 | 0.377 | macrophage migration inhibitory factor |
| HDGF | L24521 | 1.4E−07 | 0.446 | hepatoma-derived growth factor |
| SNRPE | AA733050 | 1.5E−07 | 0.483 | small nuclear ribonucleoprotein polypeptide E |
| C7orf24/MGC3077 | AI620381 | 3.9E−07 | 0.407 | chromosome 7 open reading frame 24 |
| CCT3 | X74801 | 8.1E−07 | 0.392 | chaperonin containing TCP1, subunit 3 (gamma) |
| DDR1 | U48705 | 1.2E−06 | 0.470 | discoidin domain receptor family, member 1 |
| HMGA1 | L17131 | 4.4E−06 | 0.191 | high mobility group AT-hook 1 |
| YWHAZ | U28964 | 7.8E−06 | 0.385 | tyrosine 3-monooxygenase/tryptophan 5-monooxygenase activation protein |
| TMED10 | L40397 | 9.9E−06 | 0.459 | transmembrane emp24-like trafficking protein 10 (yeast) |
| TPI1 | U47924 | 1.5E−05 | 0.446 | triosephosphate isomerase 1 |
| UBE2S | M91670 | 2.4E−05 | 0.452 | ubiquitin-conjugating enzyme E2S |
| HIST2H2AA | L19779 | 4.8E−05 | 0.282 | histone 2, H2aa |
| GPR56 | AJ011001 | 5.4E−05 | 0.445 | G protein-coupled receptor 56 |

TABLE 5-continued

Genes overexpressed in lung cancer compared to normal lung

| Gene Symbol | GenBank Accession # | P value | Ratio[1] | Description |
|---|---|---|---|---|
| SPP1 | AF052124 | 1.1E−04 | 0.080 | secreted phosphoprotein 1 (osteopontin) |
| LAPTM4B | W28186 | 1.1E−04 | 0.389 | lysosomal associated protein transmembrane 4 beta |
| MARCKSL1 | X70326 | 1.2E−04 | 0.451 | MARCKS-like 1 |
| COL3A1 | X06700 | 1.8E−04 | 0.356 | collagen, type III, alpha 1 |
| COL1A2 | K01079 | 1.9E−04 | 0.274 | collagen, type I, alpha 2 |
| COL1A2 | K01079 | 3.0E−04 | 0.211 | collagen, type I, alpha 2 |
| KRT19 | Y00503 | 7.1E−04 | 0.298 | keratin 19 |
| SPP1 | J04765 | 8.3E−04 | 0.084 | secreted phosphoprotein 1 (osteopontin) |
| MDK | M94250 | 8.5E−04 | 0.260 | midkine (neurite growth-promoting factor 2) |
| MDK | M69148 | 1.1E−03 | 0.194 | midkine (neurite growth-promoting factor 2) |
| COL5A2 | Y14690 | 1.2E−03 | 0.405 | collagen, type V, alpha 2 |
| MAGED1 | W26633 | 1.3E−03 | 0.461 | melanoma antigen family D, 1 |
| AKR1C1 /// AKR1C2 | U05861 | 1.4E−03 | 0.135 | aldo-keto reductase family 1, member C1 |
| COL1A1 | Y15915 | 1.5E−03 | 0.224 | collagen, type I, alpha 1 |
| FBL | M30448 | 1.6E−03 | 0.469 | fibrillarin |
| SFN | X57348 | 2.1E−03 | 0.369 | stratifin |
| FSCN1 | U03057 | 2.5E−03 | 0.322 | fascin homolog 1, actin-bundling protein |
| GPX2 | X53463 | 3.2E−03 | 0.060 | glutathione peroxidase 2 (gastrointestinal) |
| KRT5 | M21389 | 6.8E−03 | 0.002 | keratin 5 |
| TXNRD1 | X91247 | 9.0E−03 | 0.343 | thioredoxin reductase 1 |
| KRT6A /// KRT6C | L42611 | 9.2E−03 | 0.007 | keratin 6A /// keratin 6C |
| AKR1C3 | D17793 | 9.5E−03 | 0.172 | aldo-keto reductase family 1 |
| TXN | AI653621 | 9.6E−03 | 0.478 | thioredoxin |
| S100A2 | M87068 | 9.8E−03 | 0.071 | S100 calcium binding protein A2 |
| S100A2 | AI539439 | 1.1E−02 | 0.040 | S100 calcium binding protein A2 |
| KRT17 | Z19574 | 1.1E−02 | 0.156 | keratin 17 |
| IGFBP2 | X16302 | 1.1E−02 | 0.216 | insulin-like growth factor binding protein 2, 36 kDa |
| KRT6A /// KRT6C | L42611 | 1.2E−02 | 0.029 | keratin 6A /// keratin 6C |
| ODC1 | X16277 | 1.8E−02 | 0.273 | ornithine decarboxylase 1 |
| AKR1B10 | U37100 | 1.8E−02 | 0.017 | aldo-keto reductase family 1, member B10 (aldose reductase) |
| IGHG1 /// IGHM | AF015128 | 1.9E−02 | 0.448 | immunoglobulin heavy constant gamma 1 (G1m marker) |
| IGFBP2 | S37730 | 2.5E−02 | 0.141 | insulin-like growth factor binding protein 2, 36 kDa |
| ODC1 | M33764 | 2.6E−02 | 0.438 | ornithine decarboxylase 1 |
| IGHM | U80114 | 2.9E−02 | 0.329 | immunoglobulin heavy constant mu |
| KRT16 | AF061812 | 4.7E−02 | 0.059 | keratin 16 (focal non-epidermolytic palmoplantar keratoderma) |
| — | X72475 | 4.8E−02 | 0.447 | immunoglobulin kappa light chain variable region (IGKV gene) |

[1] Ratio of average expression level in normal lung samples/average expression level in lung cancer samples per text.

TABLE 6

Genes overexpressed in lung ADCA compared to lung SCC

| Gene Symbol | GenBank Accession # | P value | Ratio[1] | Description |
|---|---|---|---|---|
| MUC1 | J05581 | 2.6E−07 | 4.8 | mucin 1, transmembrane |
| MUC1 | J05582 | 3.6E−07 | 4.2 | mucin 1, transmembrane |
| — | HG371-HT26388 | 4.8E−07 | 3.8 | — |
| CEACAM6 | M18728 | 6.6E−07 | 6.4 | carcinoembryonic antigen-related cell adhesion molecule 6 |
| MUC1 | J05581 | 7.3E−07 | 3.8 | mucin 1, transmembrane |
| TITF1 | U43203 | 1.5E−06 | 4.9 | thyroid transcription factor 1 |
| MUC1 | M35093 | 2.2E−06 | 3.3 | mucin 1, transmembrane |
| FLJ12443 | AW024285 | 7.6E−06 | 3.8 | hypothetical protein FLJ12443 |
| — | AA156240 | 1.1E−05 | 3.6 | — |
| GPR116 | AB018301 | 1.5E−05 | 3.5 | G protein-coupled receptor 116 |
| CLDN4 | AB000712 | 2.1E−05 | 3.9 | claudin 4 |
| SFTPB | J02761 | 2.8E−05 | 2.8 | surfactant, pulmonary-associated protein B |
| TGM2 | M55153 | 4.2E−05 | 2.1 | transglutaminase 2 |
| FLJ12443 | AF052162 | 4.9E−05 | 3.8 | hypothetical protein FLJ12443 |
| SELENBP1 | U29091 | 1.1E−04 | 3.0 | selenium binding protein 1 |
| SERPINA1 | X01683 | 1.5E−04 | 3.1 | serpin peptidase inhibitor |
| KRT7 | AJ238246 | 1.6E−04 | 2.4 | keratin 7 |
| MUC1 | M21868 | 3.2E−04 | 13.6 | mucin 1, transmembrane |
| KRT18 | X12883 | 3.7E−04 | 2.0 | keratin 18 |

TABLE 6-continued

Genes overexpressed in lung ADCA compared to lung SCC

| Gene Symbol | GenBank Accession # | P value | Ratio[1] | Description |
| --- | --- | --- | --- | --- |
| RNASE1 | D26129 | 3.9E-04 | 5.3 | ribonuclease, RNase A family, 1 (pancreatic) |
| CYP2B6 /// CYP2B7P1 | M29874 | 3.9E-04 | 11.7 | cytochrome P450, family 2, subfamily B, polypeptide 6 |
| — | HG2261-HT2351 | 4.9E-04 | 2.5 | — |
| FBP1 | U21931 | 5.8E-04 | 2.0 | fructose-1,6-bisphosphatase 1 |
| SFTPB | AI820718 | 6.6E-04 | 2.6 | surfactant, pulmonary-associated protein B |
| MALL | U17077 | 7.3E-04 | 2.3 | mal, T-cell differentiation protein-like |
| CYB5 | L39945 | 9.6E-04 | 2.1 | cytochrome b-5 |
| UGDH | AF061016 | 1.3E-03 | 2.2 | UDP-glucose dehydrogenase |
| FOLR1 | U20391 | 1.6E-03 | 2.4 | folate receptor 1 (adult) |
| NNMT | U08021 | 2.1E-03 | 2.3 | nicotinamide N-methyltransferase |
| DUSP1 | X68277 | 2.4E-03 | 2.3 | dual specificity phosphatase 1 |
| WFDC2 | X63187 | 4.0E-03 | 2.4 | WAP four-disulfide core domain 2 |
| SPINK1 | AI961220 | 4.5E-03 | 23.4 | serine peptidase inhibitor, Kazal type 1 |
| MAOA | AA420624 | 4.8E-03 | 2.1 | monoamine oxidase A |
| GDF15 | AB000584 | 5.5E-03 | 2.4 | growth differentiation factor 15 |
| S100P | AA131149 | 10.0E-03 | 3.3 | S100 calcium binding protein P |
| CEACAM5 | M29540 | 1.8E-02 | 3.5 | carcinoembryonic antigen-related cell adhesion molecule 5 |
| SFTPC | J03553 | 1.9E-02 | 2.1 | surfactant, pulmonary-associated protein C |
| SCNN1A | X76180 | 2.0E-02 | 2.0 | sodium channel, nonvoltage-gated 1 alpha |
| SFTPD | X65018 | 3.1E-02 | 2.1 | surfactant, pulmonary-associated protein D |
| FOS | K00650 | 4.9E-02 | 2.4 | v-fos FBJ murine osteosarcoma viral oncogene homolog |
| PGC | M18667 | 5.0E-02 | 6.8 | progastricsin (pepsinogen C) |

[1] Ratio of average expression level in lung ADCA samples/average expression level in lung SCC samples per text.

TABLE 7

Genes overexpressed in lung SCC compared to lung ADCA

| Gene Symbol | GenBank Accession # | P value | Ratio[1] | Description |
| --- | --- | --- | --- | --- |
| TP73L | Y16961 | <1.0E-22 | 0.051 | tumor protein p73-like |
| KRT6A /// KRT6C | L42611 | <1.0E-22 | 0.054 | keratin 6A /// keratin 6C |
| KRT6A /// KRT6C | L42611 | <1.0E-22 | 0.070 | keratin 6A /// keratin 6C |
| TRIM29 | L24203 | <1.0E-22 | 0.153 | tripartite motif-containing 29 |
| SOX2 | L07335 | <1.0E-22 | 0.164 | SRY (sex determining region Y)-box 2 |
| DSP | AL031058 | <1.0E-22 | 0.349 | desmoplakin |
| KRT5 | M21389 | <1.0E-22 | 0.035 | keratin 5 |
| ABCC5 | U83661 | 1.1E-16 | 0.200 | ATP-binding cassette, sub-family C (CFTR/MRP), member 5 |
| SERPINB5 | U04313 | 1.7E-15 | 0.116 | serpin peptidase inhibitor, clade B (ovalbumin), member 5 |
| KRT13 | X14640 | 2.1E-14 | 0.109 | keratin 13 |
| ATP1B3 | U51478 | 3.2E-14 | 0.354 | ATPase, Na+/K+ transporting, beta 3 polypeptide |
| IRF6 | AL022398 | 9.4E-14 | 0.376 | interferon regulatory factor 6 |
| GPC1 | X54232 | 1.1E-13 | 0.286 | glypican 1 |
| KRT15 | X07696 | 9.6E-13 | 0.069 | keratin 15 |
| SLC6A8 | U52111 | 1.5E-12 | 0.271 | solute carrier family 6 (neurotransmitter transporter, creatine) |
| ITGA6 | X53586 | 2.1E-12 | 0.342 | integrin, alpha 6 |
| KRT14 | J00124 | 2.5E-11 | 0.021 | keratin 14 |
| KRT16 | M28439 | 4.5E-11 | 0.059 | keratin 16 |
| KRT16 | AF061812 | 2.0E-10 | 0.102 | keratin 16 |
| KRT17 | Z19574 | 5.3E-10 | 0.226 | keratin 17 |
| SPRR1A | AI923984 | 8.7E-10 | 0.077 | small proline-rich protein 1A |
| FSCN1 | U03057 | 1.3E-09 | 0.377 | fascin homolog 1, actin-bundling protein |
| S100A2 | AI539439 | 3.4E-09 | 0.153 | S100 calcium binding protein A2 |
| SFN | X57348 | 4.7E-09 | 0.461 | stratifin |
| S100A2 | M87068 | 6.2E-09 | 0.175 | S100 calcium binding protein A2 |
| SPRR1B | M19888 | 6.4E-09 | 0.033 | small proline-rich protein 1B (cornifin) |
| SFN | X57348 | 1.0E-08 | 0.484 | stratifin |
| IGFBP2 | S37730 | 1.2E-08 | 0.256 | insulin-like growth factor binding protein 2, 36 kDa |
| FABP5 | M94856 | 3.6E-08 | 0.279 | fatty acid binding protein 5 (psoriasis-associated) |
| IGFBP2 | X16302 | 1.0E-07 | 0.346 | insulin-like growth factor binding protein 2, 36 kDa |
| KRT19 | Y00503 | 2.3E-07 | 0.460 | keratin 19 |
| SPRR2D | M21302 | 5.1E-07 | 0.426 | small proline-rich protein 2D |
| PI3 | L10343 | 2.3E-06 | 0.169 | peptidase inhibitor 3, skin-derived (SKALP) |
| TFRC | X01060 | 1.1E-05 | 0.491 | transferrin receptor (p90, CD71) |
| RBP1 | M11433 | 1.1E-04 | 0.264 | retinol binding protein 1, cellular |
| S100A8 | AI126134 | 1.2E-04 | 0.296 | S100 calcium binding protein A8 (calgranulin A) |

TABLE 7-continued

| | | | | |
|---|---|---|---|---|
| Gene Symbol | GenBank Accession # | P value | Ratio[1] | Description |
| LY6D | Y12642 | 3.2E−04 | 0.028 | lymphocyte antigen 6 complex, locus D |
| ALDH3A1 | M74542 | 1.0E−02 | 0.300 | aldehyde dehydrogenase 3 family, memberA1 |

[1]Ratio of average expression level in lung ADCA samples/average expression level in lung SCC samples per text.

We claim:

1. A method for identifying a lung cell or tissue in a sample comprising
measuring the expression levels of a set of genes in a lung tumor tissue sample, wherein the set of genes comprises (i) at least one upregulated gene that is overexpressed in lung adenocarcinoma compared to lung squamous cell carcinoma, the at least one upregulated gene being selected from the genes listed in Table 6, and (ii) at least one downregulated gene that is less expressed in lung adenocarcinoma compared to lung squamous cell carcinoma, the at least one downregulated gene being selected from the genes listed in Table 7.

2. The method of claim 1, wherein the expression levels of the set of genes are measured by nucleic acid hybridization, nucleic acid amplification, or an immunological method.

3. The method of claim 1, wherein the measuring and calculating steps are performed by a diagnostic system.

4. The method of claim 2, wherein the upregulated and downregulated genes are selected as having statistically significant differences in mean expression levels.

5. The method of claim 2, wherein there is at least a 2-fold difference in mean expression levels between the at least one upregulated gene (A) and the at least one downregulated gene (B).

6. The method of claim 2, wherein two or more expression ratios $(R_1, R_2, \ldots, R_n)$ are calculated.

7. The method of claim 6, further comprising combining the two or more expression ratios $(R_1, R_2, \ldots, R_n)$.

8. The method of claim 7, wherein the step of combining the two or more expression ratios comprises calculating the geometric mean of the two or more expression ratios using the following formula: $(R_1 R_2 \ldots R_n)^{1/n}$, wherein R represents a single ratio value.

9. The method of claim 2, wherein the ratio is calculated by division of the expression level of one upregulated gene by the expression level of one downregulated gene using the formula A/B.

10. The method of claim 2, wherein the ratio is calculated by division of the expression levels of two or more upregulated genes $(A_1, A_2, \ldots, A_n)$ by the expression level of one downregulated gene (B) using the formula $((A_1 A_2 \ldots A_n)^{1/n}/B)$.

11. The method of claim 2, wherein the ratio is calculated by division of the expression level of one upregulated gene (A) by the expression levels of two or more downregulated genes $(B_1, B_2, \ldots, B_m)$ using the formula $(A/(B_1 B_2 \ldots B_m)^{1/m})$.

12. The method of claim 2, wherein the ratio is calculated by division of the expression levels of two or more upregulated genes $(A_1, A_2, \ldots, A_n)$ by the expression levels of two or more downregulated genes $(B_1, B_2, \ldots, B_m)$ using the formula $(A_1 A_2 \ldots A_n)^{1/n}/(B_1 B_2 \ldots B_m)^{1/m}$.

13. The method of claim 3, further comprising transforming the expression level data for the upregulated and/or downregulated genes prior to calculating the ratio.

14. The method of claim 13, wherein the transforming step is performed by a transformation device included in the diagnostic system.

15. The method of claim 1, further comprising identifying a treatment based on presence of the type of the lung cancer cell or tissue in the sample.

* * * * *

UNITED STATES PATENT AND TRADEMARK OFFICE
CERTIFICATE OF CORRECTION

PATENT NO. : 8,450,057 B2  
APPLICATION NO. : 12/310179  
DATED : May 28, 2013  
INVENTOR(S) : Gavin J. Gordon et al.

It is certified that error appears in the above-identified patent and that said Letters Patent is hereby corrected as shown below:

In the Claims:

Claim 1 should read:

"A method for identifying a lung cell or tissue in a sample comprising measuring the expression levels of a set of genes in a lung tumor tissue sample, wherein the set of genes comprises (i) at least one upregulated gene that is overexpressed in lung adenocarcinoma compared to lung squamous cell carcinoma, the at least one upregulated gene being selected from the genes listed in Table 6, and (ii) at least one downregulated gene that is less expressed in lung adenocarcinoma compared to lung squamous cell carcinoma, the at least one downregulated gene being selected from the genes listed in Table 7, calculating at least one ratio (R) of the expression level of the at least one upregulated gene (A) to the expression level of the at least one downregulated gene (B), and determining presence of a lung adenocarcinoma cell or tissue or presence of a lung squamous cell carcinoma cell or tissue in the sample based on the at least one ratio (R)."

Signed and Sealed this  
Sixteenth Day of July, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,450,057 B2
APPLICATION NO. : 12/310179
DATED : May 28, 2013
INVENTOR(S) : Gavin J. Gordon et al.

It is certified that error appears in the above-identified patent and that said Letters Patent is hereby corrected as shown below:

In the Specification, at column 1, immediately following the "RELATED APPLICATIONS" section, please insert:

--GOVERNMENT SUPPORT

This invention was made with Government support under Grant No. (s) DAMD17-02-2-0006 awarded by the U.S. Army Medical Research and Material Command. The Government has certain rights in this invention.--

In the Claims:

Column 43, lines 34-45, Claim 1 should read:

"A method for identifying a lung cell or tissue in a sample comprising
   measuring the expression levels of a set of genes in a lung tumor tissue sample, wherein the set of genes comprises (i) at least one upregulated gene that is overexpressed in lung adenocarcinoma compared to lung squamous cell carcinoma, the at least one upregulated gene being selected from the genes listed in Table 6, and (ii) at least one downregulated gene that is less expressed in lung adenocarcinoma compared to lung squamous cell carcinoma, the at least one downregulated gene being selected from the genes listed in Table 7,
   calculating at least one ratio (R) of the expression level of the at least one upregulated gene (A) to the expression level of the at least one downregulated gene (B), and
   determining presence of a lung adenocarcinoma cell or tissue or presence of a lung squamous cell carcinoma cell or tissue in the sample based on the at least one ratio (R)."

This certificate supersedes the Certificate of Correction issued July 16, 2013.

Signed and Sealed this
Thirteenth Day of August, 2013

Teresa Stanek Rea
*Acting Director of the United States Patent and Trademark Office*

SEQUENCE LISTING

<160> NUMBER OF SEQ ID NOS: 8

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
acttctccat ctccccgaac                                          20

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
tggtaggaca gggagtcacc                                          20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
agacaatgga atggcagctt                                          20

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 4
tgcccagaag tggcattagt                                          20

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
tccactggat gaaggatggt                                          20

```
<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
cagctgtagg ttccctggtc                                                20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
ggagcaggat gcgtatagga                                                20

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
tctgactgca cagattcttg g                                              21
```